US008153389B2

(12) United States Patent
Bergamini Moore et al.

(10) Patent No.: US 8,153,389 B2
(45) Date of Patent: Apr. 10, 2012

(54) METHODS FOR THE IDENTIFICATION OF PI3K INTERACTING MOLECULES AND FOR THE PURIFICATION OF PI3K

(75) Inventors: Giovanna Bergamini Moore, Heidelberg (DE); Andrew Cansfield, Cambridge (GB); Nigel Ramsden, Herts (GB); Gitte Neubauer, Mannheim (DE)

(73) Assignee: CellZone AG, Heidelberg (DE)

( * ) Notice: Subject to any disclaimer, the term of this patent is extended or adjusted under 35 U.S.C. 154(b) by 487 days.

(21) Appl. No.: 12/375,979

(22) PCT Filed: Aug. 3, 2007

(86) PCT No.: PCT/EP2007/006887
§ 371 (c)(1),
(2), (4) Date: Aug. 27, 2009

(87) PCT Pub. No.: WO2008/015013
PCT Pub. Date: Feb. 7, 2008

(65) Prior Publication Data
US 2010/0055711 A1    Mar. 4, 2010

(30) Foreign Application Priority Data

Aug. 3, 2006 (EP) ..................... 06016205

(51) Int. Cl.
*C12Q 1/48* (2006.01)
(52) U.S. Cl. ........................................ 435/15
(58) Field of Classification Search .............. 435/15
See application file for complete search history.

(56) References Cited

U.S. PATENT DOCUMENTS
2009/0238808 A1    9/2009  Drewes et al.

FOREIGN PATENT DOCUMENTS
| WO | WO 98/020126 | 5/1998 |
| WO | WO 03/072557 | 9/2003 |
| WO | WO 2006/051270 | 5/2006 |
| WO | WO 2006/134056 | 12/2006 |
| WO | WO 2009/098021 | 8/2009 |

OTHER PUBLICATIONS

Anieto and Gruenberg, Subcellular fractionation of tissue culture cells, Curr Protoc Protein Sci. Aug. 2004;Chapter 4:Unit 4.3.
Ausubel et al., Short Protocols in Molecular Biology. Fourth Edition, Edited by F.M. Wiley, New York, 1999; Chapter 11, Immunology, pp. 11-1 to 11-29.
Bantscheff et al., Quantitative Chemical Proteomics Reveals Mechanisms of Action of Clinical ABL Kinase Inhibitors, Nat Biotechnol. Sep. 2007;25(9):1035-1044.
Biddison, W.E., Chapter 2.2, Preparation and culture of human lymphocytes, in Current Protocols in Cell Biology, 1998, John Wiley & Sons, Inc.
Breinbauer et al., Natural product guided compound library development, Curr Med Chem. Dec. 2002;9(23):2129-45.
Camps et al., Blockade of PI3Kgamma suppresses joint inflammation and damage in mouse models of rheumatoid arthritis, Nat Med. Sep. 2005;11(9):936-943.
Cantley, The phosphoinositide 3-kinase pathway, Science. May 31, 2002;296(5573):1655-1657.
Carpenter et al., Purification and characterization of phosphoinositide 3-kinase from rat liver, J Biol Chem. Nov. 15, 1990;265(32):19704-711.
Castle, Purification of organelles from mammalian cells, Curr Protoc Protein Sci. Sep. 2004;Chapter 4:Unit 4.2.
Deora et al., A redox-triggered ras-effector interaction. Recruitment of phosphatidylinositol 3'-kinase to Ras by redox stress, J Biol Chem. Nov. 6, 1998 ;273(45):29923-8.
Drees et al., Competitive fluorescence polarization assays for the detection of phosphoinositide kinase and phosphatase activity, Comb Chem High Throughput Screen. Jun. 2003;6(4):321-30.
Edwards and Morrel, Solid-phase compound library synthesis in drug design and development, Curr Opin Drug Discov Devel. Jul. 2002;5(4):594-605.
Fruman et al., Phosphoinositide kinases, Annu Rev Biochem. 1998;67:481-507.
Fuchikami et al., A versatile high-throughput screen for inhibitors of lipid kinase activity: development of an immobilized phospholipid plate assay for phosphoinositide 3-kinase gamma, J Biomol Screen. Oct. 2002;7(5):441-50.
Goodnow, Current practices in generation of small molecule new leads, J Cell Biochem Suppl. 2001;Suppl 37:13-21.
Houtman et al., Early phosphorylation kinetics of proteins involved in proximal TCR-mediated signaling pathways, J Immunol. Aug. 15, 2004;175(4):2449-58.
Karwa and Mitra: Sample preparation for the extraction, isolation, and purification of Nuclei Acids; chapter 8 in "Sample Preparation Techniques in Analytical Chemistry", Wiley 2003, Editor: Somenath Mitra, print ISBN: 0471328456; online ISBN: 0471457817.
Kato et al., Flotillin-1 regulates IgE receptor-mediated signaling in rat basophilic leukemia (RBL-2H3) cells, J Immunol. Jul 1, 2006;177(1):147-54.
Kazlauskas et al., Phosphorylation of the PDGF receptor beta subunit creates a tight binding sight for phosphatidylinositol 3 kinase, EMBO J. Oct. 1990;9(10):3279-86.
Langer, New methods of drug delivery, Science. Sep. 28, 1990;249(4976):1527-33.
Mann et al., Analysis of proteins and proteomes by mass spectrometry, Annu Rev Biochem. 2001;70:437-73.
Merlot et al., Fragment analysis in small molecule discovery, Curr Opin Drug Discov Devel. May 2002;5(3):391-9. Ohashi and Woodgett, Modulating autoimmunity: pick your PI3 kinase, Nat Med. Sep. 2005;11(9):924-5.
Okishio et al., Identification of tyrosine residues involved in ligand recognition by the phosphatdylinositol 3-kinase Scr homology 3 domain: Circular dichroism and UV resonance Raman studies, Biochemistry. Dec. 25, 2001;40(51):15797-804.
Perkins et al., Probability-based protein identification by searching sequence databases using mass spectrometry data, Electrophoresis. Dec. 1999;20(18):3551-67.
Petty, Unit 5.1: Overview of the Physical State of Proteins Within Cells, Current Protocols in Cell Biology, (1998) 5.1.1-5.1.10.
Pomel et al., Furan-2-ylmethylene thiazolidinediones as novel, potent, and selective inhibitors of phosphoinositide 3-kinase gamma, J Med Chem. Jun. 29, 2006;49(13):3857-71.
Sasaki et al., Colorectal carcinomas in mice lacking the catalytic subunit of PI(3)Kgamma, Nature. Aug. 24, 2004;406(6798):897-902.
Schutz-Geschwendener et al., 2004. Quantitative, two-color Western blot detection with infrared fluorescence. Published May 2004 by LI-COR Biosciences, www.licor.com.

(Continued)

*Primary Examiner* — Maryam Monshipouri
(74) *Attorney, Agent, or Firm* — Kristina Bieker-Brady; Clark & Elbing LLP

(57) ABSTRACT

The present invention relates to methods for the identification of a PI3K interacting compound using phenylthiazole ligand 1.

21 Claims, 9 Drawing Sheets

OTHER PUBLICATIONS

Figure 1:
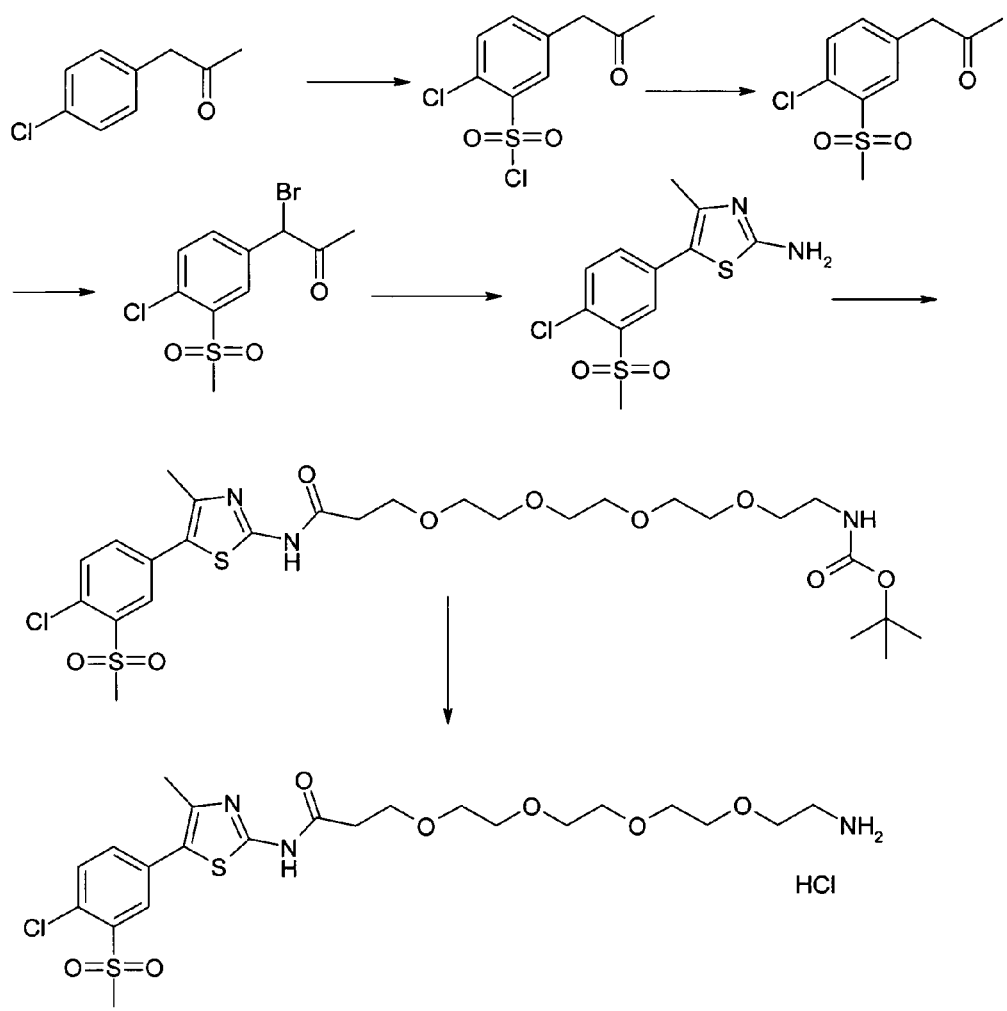

Shevchenko et al., Mass spectrometric sequencing of proteins silver-stained polyacrylamide gels, Anal Chem. Mar. 1, 1996;68(5):850-858.

Subramanian, Immunoaffinity chromatography, Mol Biotechnol. Jan. 2002;20(1):41-7.

Vlahos et al., A specific inhibitor of phosphatidylinositol 3-kinase, 2-(4-morpholinyl)-8-phenyl-4H-1-benzopyran-4- one (LY294002), J Biol Chem. Feb. 18, 1994;269(7):5241-8.

Walker et al., Structural determinants of phosphoinositide 3-kinase inhibtion by Wortmannin, LY294002, quercetin, myricetin, and staurosporine, Mol Cell. Oct. 2000;6(4):909-19.

Wetzker and Rommel, Phosphoinositide 3-kinases as targets for therapeutic intervention, Curr Pharm Des. 2004;10(16):1915-1922.

Wingfield, P. T., Chapter 5, Production of Recombinant Proteins, in Current Protocols in Protein Science, 2002 5.0.1-5.0.3.

Wolff et al., Automated high content screening for phosphoinositide 3 kinase inhibition using an AKT 1 redistribution assay, Comb Chem High Throughput Screen. Jun. 2006;9(5):339-50.

Wu and Wu, Receptor-mediated in vitro gene transformation by a soluble DNA carrier system, J Biol Chem. Apr. 5, 1987;262(10):4429-32.

Wu et al., Comparative study of three proteomic quantitative methods, DIGE, cICAT, and iTRAQ, using 2D gel-or LC-MALDI TOF/TOF, J Proteome Res. Mar. 2006;5(3):651-8.

Figure 4

```
   1 MELENYKQPV VLREDNCRRR RRMKPRSAAA SLSSMELIPI EFVLPTSQRK
  51 CKSPETALLH VAGHGNVEQM KAQVWLRALE TSVAADFYHR LGPHHFLLLY
 101 QKKGQWYEIY DKYQVVQTLD CLRYWKATHR SPGQIHLVQR HPPSEESQAF
 151 QRQLTALIGY DVTDVSNVHD DELEFTRRGL VTPRMAEVAS RDPKLYAMHP
 201 WVTSKPLPEY LWKKIANNCI FIVIHRSTTS QTIKVSPDDT PGAILQSFFT
 251 KMAKKKSLMD IPESQSEQDF VLRVCGRDEY LVGETPIKNF QWVRHCLKNG
 301 EEIHVVLDTP PDPALDEVRK EEWPLVDDCT GVTGYHEQLT IHGKDHESVF
 351 TVSLWDCDRK FRVKIRGIDI PVLPRNTDLT VFVEANIQHG QQVLCQRRTS
 401 PKPFTEEVLW NVWLEFSIKI KDLPKGALLN LQIYCGKAPA LSSKASAESP
 451 SSESKGKVQL LYYVNLLLID HRFLLRRGEY VLHMWQISGK GEDQGSFNAD
 501 KLTSATNPDK ENSMSISILL DNYCHPIALP KHQPTPDPEG DRVRAEMPNQ
 551 LRKQLEAIIA TDPLNPLTAE DKELLWHFRY ESLKHPKAYP KLFSSVKWGQ
 601 QEIVAKTYQL LARREVWDQS ALDVGLTMQL LDCNFSDENV RAIAVQKLES
 651 LEDDDVLHYL LQLVQAVKFE PYHDSALARF LLKRGLRNKR IGHFLFWFLR
 701 SEIAQSRHYQ QRFAVILEAY LRGCGTAMLH DFTQQVQVIE MLQKVTLDIK
 751 SLSAEKYDVS SQVISQLKQK LENLQNSQLP ESFRVPYDPG LKAGALAIEK
 801 CKVMASKKKP LWLEFKCADP TALSNETIGI IFKHGDDLRQ DMLILQILRI
 851 MESIWETESL DLCLLPYGCI STGDKIGMIE IVKDATTIAK IQQSTVGNTG
 901 AFKDEVLNHW LKEKSPTEEK FQAAVERFVY SCAGYCVATF VLGIGDRHND
 951 NIMITETGNL FHIDFGHILG NYKSFLGINK ERVPFVLTPD FLFVMGTSGK
1001 KTSPHFQKFQ DICVKAYLAL RHHTNLLIIL FSMMLMTGMP QLTSKEDIEY
1051 IRDALTVGKN EEDAKKYFLD QIEVCRDKGW TVQFNWFLHL VLGIKQGEKH
1101 SA
```

Figure 5

```
   1    MPPGVDCPME  FWTKEENQSV  VVDFLLPTGV  YLNFPVSRNA  NLSTIKQLLW
  51    HRAQYEPLFH  MLSGPEAYVF  TCINQTAEQQ  ELEDEQRRLC  DVQPFLPVLR
 101    LVAREGDRVK  KLINSQISLL  IGKGLHEFDS  LCDPEVNDFR  AKMCQFCEEA
 151    AARRQQLGWE  AWLQYSFPLQ  LEPSAQTWGP  GTLRLPNRAL  LVNVKFEGSE
 201    ESFTFQVSTK  DVPLALMACA  LRKKATVFRQ  PLVEQPEDYT  LQVNGRHEYL
 251    YGSYPLCQFQ  YICSCLHSGL  TPHLTMVHSS  SILAMRDEQS  NPAPQVQKPR
 301    AKPPPIPAKK  PSSVSLWSLE  QPFRIELIQG  SKVNADERMK  LVVQAGLFHG
 351    NEMLCKTVSS  SEVSVCSEPV  WKQRLEFDIN  ICDLPRMARL  CFALYAVIEK
 401    AKKARSTKKK  SKKADCPIAW  ANLMLFDYKD  QLKTGERCLY  MWPSVPDEKG
 451    ELLNPTGTVR  SNPNTDSAAA  LLICLPEVAP  HPVYYPALEK  ILELGRHSEC
 501    VHVTEEEQLQ  LREILERRGS  GELYEHEKDL  VWKLRHEVQE  HFPEALARLL
 551    LVTKWNKHED  VAQMLYLLCS  WPELPVLSAL  ELLDFSFPDC  HVGSFAIKSL
 601    RKLTDDELFQ  YLLQLVQVLK  YESYLDCELT  KFLLDRALAN  RKIGHFLFWH
 651    LRSEMHVPSV  ALRFGLILEA  YCRGRTHHMK  VLMKQGEALS  KLKALNDFVK
 701    LSSQKTPKPQ  TKELMHLCMR  QEAYLEALSH  LQSPLDPSTL  LAEVCVEQCT
 751    FMDSKMKPLW  IMYSNEEAGS  GGSVGIIFKN  GDDLRQDMLT  LQMIQLMDVL
 801    WKQEGLDLRM  TPYGCLPTGD  RTGLIEVVLR  SDTIANIQLN  KSNMAATAAF
 851    NKDALLNWLK  SKNPGEALDR  AIEEFTLSCA  GYCVATYVLG  IGDRHSDNIM
 901    IRESGQLFHI  DFGHFLGNFK  TKFGINRERV  PFILTYDFVH  VIQQGKTNNS
 951    EKFERFRGYC  ERAYTILRRH  GLLFLHLFAL  MRAAGLPELS  CSKDIQYLKD
1001    SLALGKTEEE  ALKHFRVKFN  EALRESWKTK  VNWLAHNVSK  DNRQ
```

Figure 7:
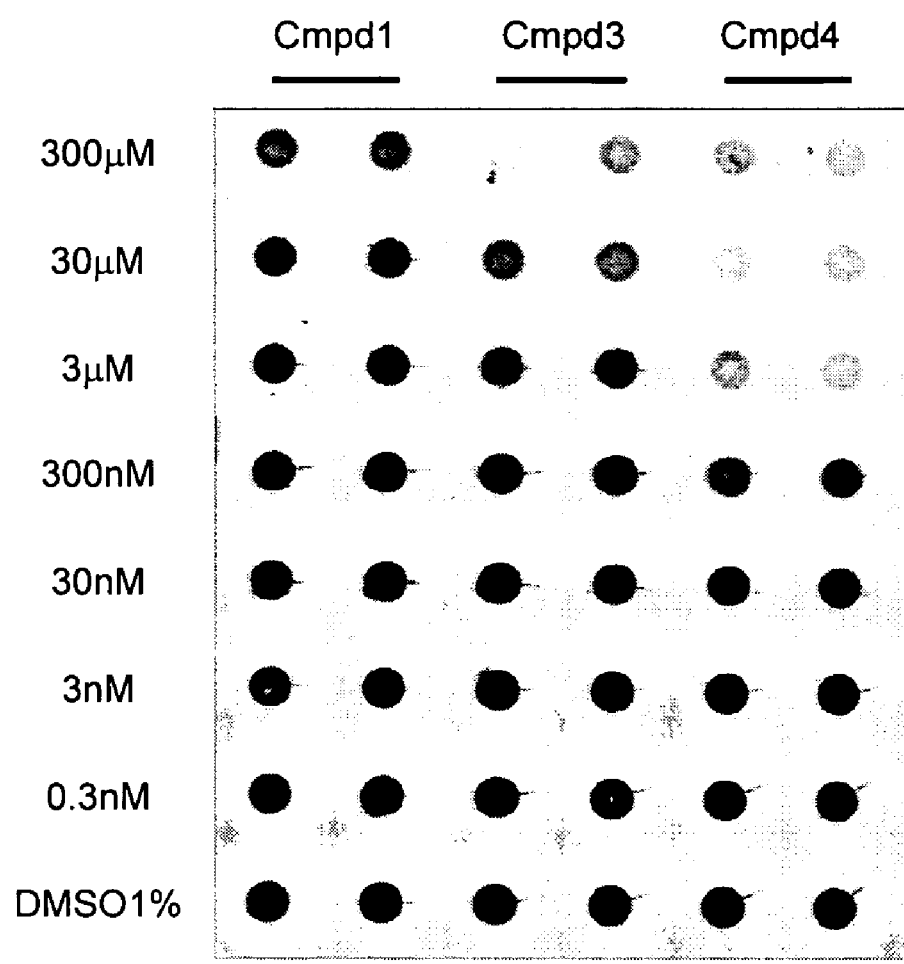

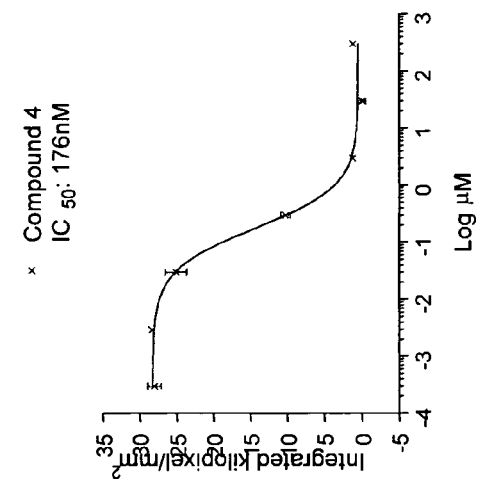
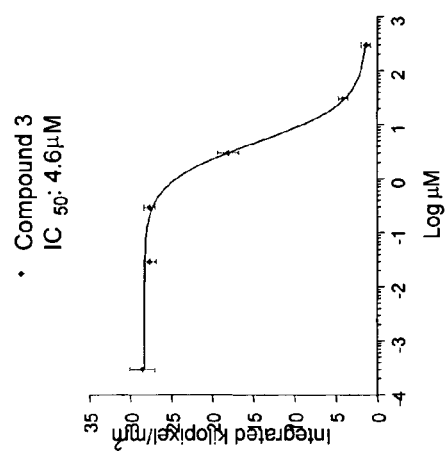
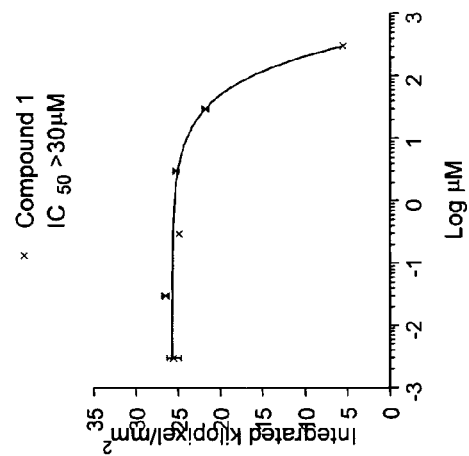
Figure 7 B

```
                         SEQUENCE LISTING

<160> NUMBER OF SEQ ID NOS: 2

<210> SEQ ID NO 1
<211> LENGTH: 1102
<212> TYPE: PRT
<213> ORGANISM: Homo sapiens

<400> SEQUENCE: 1

Met Glu Leu Glu Asn Tyr Lys Gln Pro Val Val Leu Arg Glu Asp Asn
1               5                   10                  15

Cys Arg Arg Arg Arg Met Lys Pro Arg Ser Ala Ala Ala Ser Leu
                20                  25                  30

Ser Ser Met Glu Leu Ile Pro Ile Glu Phe Val Leu Pro Thr Ser Gln
            35                  40                  45

Arg Lys Cys Lys Ser Pro Glu Thr Ala Leu Leu His Val Ala Gly His
        50                  55                  60

Gly Asn Val Glu Gln Met Lys Ala Gln Val Trp Leu Arg Ala Leu Glu
65                  70                  75                  80

Thr Ser Val Ala Ala Asp Phe Tyr His Arg Leu Gly Pro His His Phe
                85                  90                  95

Leu Leu Leu Tyr Gln Lys Lys Gly Gln Trp Tyr Glu Ile Tyr Asp Lys
            100                 105                 110

Tyr Gln Val Val Gln Thr Leu Asp Cys Leu Arg Tyr Trp Lys Ala Thr
        115                 120                 125

His Arg Ser Pro Gly Gln Ile His Leu Val Gln Arg His Pro Pro Ser
    130                 135                 140

Glu Glu Ser Gln Ala Phe Gln Arg Gln Leu Thr Ala Leu Ile Gly Tyr
145                 150                 155                 160

Asp Val Thr Asp Val Ser Asn Val His Asp Asp Glu Leu Glu Phe Thr
                165                 170                 175

Arg Arg Gly Leu Val Thr Pro Arg Met Ala Glu Val Ala Ser Arg Asp
            180                 185                 190

Pro Lys Leu Tyr Ala Met His Pro Trp Val Thr Ser Lys Pro Leu Pro
        195                 200                 205

Glu Tyr Leu Trp Lys Lys Ile Ala Asn Asn Cys Ile Phe Ile Val Ile
    210                 215                 220

His Arg Ser Thr Thr Ser Gln Thr Ile Lys Val Ser Pro Asp Asp Thr
225                 230                 235                 240

Pro Gly Ala Ile Leu Gln Ser Phe Phe Thr Lys Met Ala Lys Lys Lys
                245                 250                 255

Ser Leu Met Asp Ile Pro Glu Ser Gln Ser Glu Gln Asp Phe Val Leu
            260                 265                 270
```

-continued

```
Arg Val Cys Gly Arg Asp Glu Tyr Leu Val Gly Thr Pro Ile Lys
        275                 280                 285
Asn Phe Gln Trp Val Arg His Cys Leu Lys Asn Gly Glu Glu Ile His
290                 295                 300
Val Val Leu Asp Thr Pro Pro Asp Pro Ala Leu Asp Glu Val Arg Lys
305                 310                 315                 320
Glu Glu Trp Pro Leu Val Asp Asp Cys Thr Gly Val Thr Gly Tyr His
                325                 330                 335
Glu Gln Leu Thr Ile His Gly Lys Asp His Glu Ser Val Phe Thr Val
                340                 345                 350
Ser Leu Trp Asp Cys Asp Arg Lys Phe Arg Val Lys Ile Arg Gly Ile
                355                 360                 365
Asp Ile Pro Val Leu Pro Arg Asn Thr Asp Leu Thr Val Phe Val Glu
370                 375                 380
Ala Asn Ile Gln His Gly Gln Gln Val Leu Cys Gln Arg Arg Thr Ser
385                 390                 395                 400
Pro Lys Pro Phe Thr Glu Val Leu Trp Asn Val Trp Leu Glu Phe
                405                 410                 415
Ser Ile Lys Ile Lys Asp Leu Pro Lys Gly Ala Leu Leu Asn Leu Gln
                420                 425                 430
Ile Tyr Cys Gly Lys Ala Pro Ala Leu Ser Ser Lys Ala Ser Ala Glu
                435                 440                 445
Ser Pro Ser Ser Glu Ser Lys Gly Lys Val Gln Leu Leu Tyr Tyr Val
                450                 455                 460
Asn Leu Leu Leu Ile Asp His Arg Phe Leu Leu Arg Arg Gly Glu Tyr
465                 470                 475                 480
Val Leu His Met Trp Gln Ile Ser Gly Lys Gly Glu Asp Gln Gly Ser
                485                 490                 495
Phe Asn Ala Asp Lys Leu Thr Ser Ala Thr Asn Pro Asp Lys Glu Asn
                500                 505                 510
Ser Met Ser Ile Ser Ile Leu Leu Asp Asn Tyr Cys His Pro Ile Ala
                515                 520                 525
Leu Pro Lys His Gln Pro Thr Pro Asp Pro Glu Gly Asp Arg Val Arg
                530                 535                 540
Ala Glu Met Pro Asn Gln Leu Arg Lys Gln Leu Glu Ala Ile Ile Ala
545                 550                 555                 560
Thr Asp Pro Leu Asn Pro Leu Thr Ala Glu Asp Lys Glu Leu Leu Trp
                565                 570                 575
His Phe Arg Tyr Glu Ser Leu Lys His Pro Lys Ala Tyr Pro Lys Leu
                580                 585                 590
Phe Ser Ser Val Lys Trp Gly Gln Gln Glu Ile Val Ala Lys Thr Tyr
                595                 600                 605
Gln Leu Leu Ala Arg Arg Glu Val Trp Asp Gln Ser Ala Leu Asp Val
610                 615                 620
Gly Leu Thr Met Gln Leu Leu Asp Cys Asn Phe Ser Asp Glu Asn Val
625                 630                 635                 640
Arg Ala Ile Ala Val Gln Lys Leu Glu Ser Leu Glu Asp Asp Val
                645                 650                 655
Leu His Tyr Leu Leu Gln Leu Val Gln Ala Val Lys Phe Glu Pro Tyr
                660                 665                 670
His Asp Ser Ala Leu Ala Arg Phe Leu Leu Lys Arg Gly Leu Arg Asn
                675                 680                 685
Lys Arg Ile Gly His Phe Leu Phe Trp Phe Leu Arg Ser Glu Ile Ala
                690                 695                 700
```

```
Gln Ser Arg His Tyr Gln Gln Arg Phe Ala Val Ile Leu Glu Ala Tyr
705                 710                 715                 720

Leu Arg Gly Cys Gly Thr Ala Met Leu His Asp Phe Thr Gln Gln Val
            725                 730                 735

Gln Val Ile Glu Met Leu Gln Lys Val Thr Leu Asp Ile Lys Ser Leu
        740                 745                 750

Ser Ala Glu Lys Tyr Asp Val Ser Ser Gln Val Ile Ser Gln Leu Lys
    755                 760                 765

Gln Lys Leu Glu Asn Leu Gln Asn Ser Gln Leu Pro Glu Ser Phe Arg
770                 775                 780

Val Pro Tyr Asp Pro Gly Leu Lys Ala Gly Ala Leu Ala Ile Glu Lys
785                 790                 795                 800

Cys Lys Val Met Ala Ser Lys Lys Pro Leu Trp Leu Glu Phe Lys
                805                 810                 815

Cys Ala Asp Pro Thr Ala Leu Ser Asn Glu Thr Ile Gly Ile Phe
                820                 825                 830

Lys His Gly Asp Asp Leu Arg Gln Asp Met Leu Ile Leu Gln Ile Leu
            835                 840                 845

Arg Ile Met Glu Ser Ile Trp Glu Thr Glu Ser Leu Asp Leu Cys Leu
        850                 855                 860

Leu Pro Tyr Gly Cys Ile Ser Thr Gly Asp Lys Ile Gly Met Ile Glu
865                 870                 875                 880

Ile Val Lys Asp Ala Thr Thr Ile Ala Lys Ile Gln Gln Ser Thr Val
            885                 890                 895

Gly Asn Thr Gly Ala Phe Lys Asp Glu Val Leu Asn His Trp Leu Lys
            900                 905                 910

Glu Lys Ser Pro Thr Glu Glu Lys Phe Gln Ala Ala Val Glu Arg Phe
        915                 920                 925

Val Tyr Ser Cys Ala Gly Tyr Cys Val Ala Thr Phe Val Leu Gly Ile
    930                 935                 940

Gly Asp Arg His Asn Asp Asn Ile Met Ile Thr Glu Thr Gly Asn Leu
945                 950                 955                 960

Phe His Ile Asp Phe Gly His Ile Leu Gly Asn Tyr Lys Ser Phe Leu
                965                 970                 975

Gly Ile Asn Lys Glu Arg Val Pro Phe Val Leu Thr Pro Asp Phe Leu
            980                 985                 990

Phe Val Met Gly Thr Ser Gly Lys Lys Thr Ser Pro His Phe Gln Lys
        995                 1000                1005

Phe Gln Asp Ile Cys Val Lys Ala Tyr Leu Ala Leu Arg His His
    1010                1015                1020

Thr Asn Leu Leu Ile Ile Leu Phe Ser Met Met Leu Met Thr Gly
    1025                1030                1035

Met Pro Gln Leu Thr Ser Lys Glu Asp Ile Glu Tyr Ile Arg Asp
    1040                1045                1050

Ala Leu Thr Val Gly Lys Asn Glu Glu Asp Ala Lys Lys Tyr Phe
    1055                1060                1065

Leu Asp Gln Ile Glu Val Cys Arg Asp Lys Gly Trp Thr Val Gln
    1070                1075                1080

Phe Asn Trp Phe Leu His Leu Val Leu Gly Ile Lys Gln Gly Glu
    1085                1090                1095

Lys His Ser Ala
    1100
```

```
<210> SEQ ID NO 2
<211> LENGTH: 1044
<212> TYPE: PRT
<213> ORGANISM: Homo sapiens

<400> SEQUENCE: 2

Met Pro Pro Gly Val Asp Cys Pro Met Glu Phe Trp Thr Lys Glu Glu
1               5                   10                  15

Asn Gln Ser Val Val Asp Phe Leu Leu Pro Thr Gly Val Tyr Leu
            20                  25                  30

Asn Phe Pro Val Ser Arg Asn Ala Asn Leu Ser Thr Ile Lys Gln Leu
        35                  40                  45

Leu Trp His Arg Ala Gln Tyr Glu Pro Leu Phe His Met Leu Ser Gly
    50                  55                  60

Pro Glu Ala Tyr Val Phe Thr Cys Ile Asn Gln Thr Ala Glu Gln Gln
65                  70                  75                  80

Glu Leu Glu Asp Glu Gln Arg Arg Leu Cys Asp Val Gln Pro Phe Leu
                85                  90                  95

Pro Val Leu Arg Leu Val Ala Arg Glu Gly Asp Arg Val Lys Lys Leu
            100                 105                 110

Ile Asn Ser Gln Ile Ser Leu Leu Ile Gly Lys Gly Leu His Glu Phe
        115                 120                 125

Asp Ser Leu Cys Asp Pro Glu Val Asn Asp Phe Arg Ala Lys Met Cys
    130                 135                 140

Gln Phe Cys Glu Glu Ala Ala Ala Arg Arg Gln Gln Leu Gly Trp Glu
145                 150                 155                 160

Ala Trp Leu Gln Tyr Ser Phe Pro Leu Gln Leu Glu Pro Ser Ala Gln
                165                 170                 175

Thr Trp Gly Pro Gly Thr Leu Arg Leu Pro Asn Arg Ala Leu Leu Val
            180                 185                 190

Asn Val Lys Phe Glu Gly Ser Glu Glu Ser Phe Thr Phe Gln Val Ser
        195                 200                 205

Thr Lys Asp Val Pro Leu Ala Leu Met Ala Cys Ala Leu Arg Lys Lys
    210                 215                 220

Ala Thr Val Phe Arg Gln Pro Leu Val Glu Gln Pro Glu Asp Tyr Thr
225                 230                 235                 240

Leu Gln Val Asn Gly Arg His Glu Tyr Leu Tyr Gly Ser Tyr Pro Leu
                245                 250                 255

Cys Gln Phe Gln Tyr Ile Cys Ser Cys Leu His Ser Gly Leu Thr Pro
            260                 265                 270

His Leu Thr Met Val His Ser Ser Ile Leu Ala Met Arg Asp Glu
        275                 280                 285

Gln Ser Asn Pro Ala Pro Gln Val Gln Lys Pro Arg Ala Lys Pro Pro
    290                 295                 300

Pro Ile Pro Ala Lys Lys Pro Ser Ser Val Ser Leu Trp Ser Leu Glu
305                 310                 315                 320

Gln Pro Phe Arg Ile Glu Leu Ile Gln Gly Ser Lys Val Asn Ala Asp
                325                 330                 335

Glu Arg Met Lys Leu Val Val Gln Ala Gly Leu Phe His Gly Asn Glu
            340                 345                 350

Met Leu Cys Lys Thr Val Ser Ser Ser Glu Val Ser Val Cys Ser Glu
        355                 360                 365

Pro Val Trp Lys Gln Arg Leu Glu Phe Asp Ile Asn Ile Cys Asp Leu
    370                 375                 380

Pro Arg Met Ala Arg Leu Cys Phe Ala Leu Tyr Ala Val Ile Glu Lys
```

```
             385                 390                 395                 400
Ala Lys Lys Ala Arg Ser Thr Lys Lys Ser Lys Lys Ala Asp Cys
                405                 410                 415

Pro Ile Ala Trp Ala Asn Leu Met Leu Phe Asp Tyr Lys Asp Gln Leu
                420                 425                 430

Lys Thr Gly Glu Arg Cys Leu Tyr Met Trp Pro Ser Val Pro Asp Glu
                435                 440                 445

Lys Gly Glu Leu Leu Asn Pro Thr Gly Thr Val Arg Ser Asn Pro Asn
    450                 455                 460

Thr Asp Ser Ala Ala Leu Leu Ile Cys Leu Pro Glu Val Ala Pro
465                 470                 475                 480

His Pro Val Tyr Tyr Pro Ala Leu Glu Lys Ile Leu Glu Leu Gly Arg
                485                 490                 495

His Ser Glu Cys Val His Val Thr Glu Glu Gln Leu Gln Leu Arg
                500                 505                 510

Glu Ile Leu Glu Arg Arg Gly Ser Gly Glu Leu Tyr Glu His Glu Lys
                515                 520                 525

Asp Leu Val Trp Lys Leu Arg His Glu Val Gln Glu His Phe Pro Glu
    530                 535                 540

Ala Leu Ala Arg Leu Leu Leu Val Thr Lys Trp Asn Lys His Glu Asp
545                 550                 555                 560

Val Ala Gln Met Leu Tyr Leu Leu Cys Ser Trp Pro Glu Leu Pro Val
                565                 570                 575

Leu Ser Ala Leu Glu Leu Leu Asp Phe Ser Phe Pro Asp Cys His Val
                580                 585                 590

Gly Ser Phe Ala Ile Lys Ser Leu Arg Lys Leu Thr Asp Asp Glu Leu
                595                 600                 605

Phe Gln Tyr Leu Leu Gln Leu Val Gln Val Leu Lys Tyr Glu Ser Tyr
    610                 615                 620

Leu Asp Cys Glu Leu Thr Lys Phe Leu Leu Asp Arg Ala Leu Ala Asn
625                 630                 635                 640

Arg Lys Ile Gly His Phe Leu Phe Trp His Leu Arg Ser Glu Met His
                645                 650                 655

Val Pro Ser Val Ala Leu Arg Phe Gly Leu Ile Leu Glu Ala Tyr Cys
                660                 665                 670

Arg Gly Arg Thr His His Met Lys Val Leu Met Lys Gln Gly Glu Ala
                675                 680                 685

Leu Ser Lys Leu Lys Ala Leu Asn Asp Phe Val Lys Leu Ser Ser Gln
    690                 695                 700

Lys Thr Pro Lys Pro Gln Thr Lys Glu Leu Met His Leu Cys Met Arg
705                 710                 715                 720

Gln Glu Ala Tyr Leu Glu Ala Leu Ser His Leu Gln Ser Pro Leu Asp
                725                 730                 735

Pro Ser Thr Leu Leu Ala Glu Val Cys Val Glu Gln Cys Thr Phe Met
                740                 745                 750

Asp Ser Lys Met Lys Pro Leu Trp Ile Met Tyr Ser Asn Glu Glu Ala
                755                 760                 765

Gly Ser Gly Gly Ser Val Gly Ile Ile Phe Lys Asn Gly Asp Asp Leu
                770                 775                 780

Arg Gln Asp Met Leu Thr Leu Gln Met Ile Gln Leu Met Asp Val Leu
785                 790                 795                 800

Trp Lys Gln Glu Gly Leu Asp Leu Arg Met Thr Pro Tyr Gly Cys Leu
                805                 810                 815
```

-continued

```
Pro Thr Gly Asp Arg Thr Gly Leu Ile Glu Val Val Leu Arg Ser Asp
            820                 825                 830

Thr Ile Ala Asn Ile Gln Leu Asn Lys Ser Asn Met Ala Ala Thr Ala
            835                 840                 845

Ala Phe Asn Lys Asp Ala Leu Leu Asn Trp Leu Lys Ser Lys Asn Pro
850                 855                 860

Gly Glu Ala Leu Asp Arg Ala Ile Glu Phe Thr Leu Ser Cys Ala
865                 870                 875                 880

Gly Tyr Cys Val Ala Thr Tyr Val Leu Gly Ile Gly Asp Arg His Ser
                885                 890                 895

Asp Asn Ile Met Ile Arg Glu Ser Gly Gln Leu Phe His Ile Asp Phe
                900                 905                 910

Gly His Phe Leu Gly Asn Phe Lys Thr Lys Phe Gly Ile Asn Arg Glu
            915                 920                 925

Arg Val Pro Phe Ile Leu Thr Tyr Asp Phe Val His Val Ile Gln Gln
            930                 935                 940

Gly Lys Thr Asn Asn Ser Glu Lys Phe Glu Arg Phe Arg Gly Tyr Cys
945                 950                 955                 960

Glu Arg Ala Tyr Thr Ile Leu Arg Arg His Gly Leu Leu Phe Leu His
                965                 970                 975

Leu Phe Ala Leu Met Arg Ala Ala Gly Leu Pro Glu Leu Ser Cys Ser
                980                 985                 990

Lys Asp Ile Gln Tyr Leu Lys Asp  Ser Leu Ala Leu Gly  Lys Thr Glu
                995                1000                1005

Glu Glu  Ala Leu Lys His Phe  Arg Val Lys Phe Asn  Glu Ala Leu
    1010                1015                1020

Arg Glu  Ser Trp Lys Thr Lys  Val Asn Trp Leu Ala  His Asn Val
    1025                1030                1035

Ser Lys  Asp Asn Arg Gln
    1040
```

METHODS FOR THE IDENTIFICATION OF PI3K INTERACTING MOLECULES AND FOR THE PURIFICATION OF PI3K

CROSS-REFERENCE TO RELATED APPLICATIONS

This application is the U.S. National Stage of International Application No. PCT/EP2007/006887, filed Aug. 3, 2007, which in turn, claims the benefit of European Application No. 06016205.4, filed Aug. 3, 2006, each of which is incorporated by reference.

The present invention relates to methods for the identification of PI3K interacting molecules and for the purification of PI3K using phenylthiazole ligand 1 as a ligand for PI3K. Furthermore, the present invention relates to pharmaceutical compositions comprising said interacting molecules e.g. for the treatment of cancer, metabolic diseases or autoimmune/inflammatory disorders.

Kinases catalyze the phosphorylation of proteins, lipids, sugars, nucleosides and other cellular metabolites and play key roles in all aspects of eukryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Inappropriately high protein kinase activity is involved in many diseases including cancer, metabolic diseases and autoimmune/inflammatory disorders. This can be caused either directly or indirectly by the failure of control mechanisms due to mutation, overexpression or inappropriate activation of the enzyme. In all of these instances, selective inhibition of the kinase is expected to have a beneficial effect.

One group of lipid kinases that has become a recent focus of drug discovery is the phosphoinositide 3-kinase (PI3K) family. Members of the PI3K family are lipid kinases that catalyse the transfer of the gamma-phosphate from ATP to the 3'-hydroxyl group of phophatidylinositol and its derivatives, collectively called phosphoinositides. Eight members (isoforms) of the PI3K family have been isolated from mammalian cells so far and grouped into three classes according to their primary structure and substrate specificity (class IA: PI3K alpha, beta and delta; class IB: PI3K gamma; class II: PI3KC2 alpha, beta and gamma; class III: Vps34 yeast homologue) (Fruman et al., 1998. Phosphoinositide kinases. Annual Review Biochemistry 67, 481-507; Cantley, L. C., 2002, Science 296, 1655-1657).

Mammalian cells are known to express three isoforms of the catalytic subunit of PI3K IA class (p110 alpha, p110 beta and p110 delta, synonym "PI3K delta"). Class IB contains only one member (catalytic subunit) which has been named p110gamma or PI3K gamma. In addition to its lipid kinase activity PI3K gamma exhibits also a serine/threonine protein kinase activity as demonstrated by autophosphorylation.

The study of genetically manipulated mice in which the genes encoding PI3K gamma or delta were deleted give important information about the physiological function of these kinases and their potential utility as drug targets. Mice lacking PI3K gamma or delta are viable and exhibit distinctive phenotypes suggesting several potential therapeutic indications. PI3K gamma appears to be a major mediator of the innate immune system. For example, PI3K gamma deficient macrophages and neutrophilic granulocytes display an impaired ability to infiltrate the inflamed peritoneum. Mast cells represent another cell type affected in PI3K gamma deficient mice. The phenotype of mice lacking PI3K delta is characterized by an impairment of lymphocyte functions and point to a dominant function in the control of the adaptive immune response (Wetzker and Rommel, Current Pharmaceutical Design, 2004, 10, 1915-1922).

In contrast to the widely expressed PI3K alpha and beta isoforms the hematopoietic specific isoforms PI3K gamma and delta suggest important therapeutic indications. Both isoforms appear as ideal targets for the treatment of autoimmune/inflammatory diseases mediated by hyperactive phagocytes, mast cells, B- and T-lymphocytes (e.g. rheumatoid arthritis, asthma or allergic reactions). In order to avoid unwanted side effects highly isoform selective inhibitors are necessary (Ohasi and Woodgett 2005, Nature Medicine 11, 924-925).

One prerequisite for the identification and characterization of PI3K inhibitors is the provision of suitable assays, preferably physiological forms of the protein target. In the art, several strategies have been proposed to address this issue.

Conventionally, PI3K lipid kinase activity can be measured using purified or recombinant enzyme in a solution-based assay with phospholipid vesicles. The reaction is terminated by the addition of acidified organic solvents and subsequent phase separation by extraction or thin layer chromatography analysis (Carpenter et al., 1990, J. Biol. Chem. 265, 19704-19711).

Another assay described in the art is based on the phosphate transfer from radiolabeled ATP to phosphatidylinositol immobilized on plates. This assay type also uses recombinant PI3K gamma enzyme but can be performed in a high throughput mode (Fuchikami et al., 2002, J. Biomol. Screening 7, 441-450).

Yet another biochemical screening assay is based on a competitive fluorescence polarization (FP) format using fluorophore-labeled phosphoinositide (Drees et al., 2003, Comb. Chem. High Throughput Screening 6, 321-330).

Finally, a cell-based Akt-EGFP redistribution assay was reported based on fluorescence microscopic imaging and automated image analysis. To this end Chinese Hamster Ovary (CHO) cells were stably transfected with the human insulin receptor and an Akt1-enhanced green fluorescent protein (EGFP) fusion construct. After stimulation with insulin-like growth factor-1 (IGF-1) PI3K was activated and the Akt1-EGFP protein was recruited to the cell membrane. The validation of the redistribution assay with PI3K isoform selective inhibitors showed that PI3K alpha is the main isoform activated in CHO host cells after IGF-1 stimulation (Wolff et al., Comb. Chem. High Throughput Screen. 9, 339-350).

In view of the above, there is a need for providing effective methods for the identification and selectivity profiling of PI3K interacting compounds as well as for methods for the purification of PI3K.

To comply with this need, the invention provides in a first aspect a method for the identification of a PI3K interacting compound, comprising the steps of
  a) providing a protein preparation containing PI3K,
  b) contacting the protein preparation with phenylthiazole ligand 1 immobilized on a solid support under conditions allowing the formation of an phenylthiazole ligand 1-PI3K complex,
  c) incubating the phenylthiazole ligand 1-PI3K complex with a given compound, and
  d) determining whether the compound is able to separate PI3K from the immobilized phenylthiazole ligand 1.

In a second aspect, the present invention relates to a method for the identification of a PI3K interacting compound, comprising the steps of
a) providing a protein preparation containing PI3K,
b) contacting the protein preparation with phenylthiazole ligand 1 immobilized on a solid support and with a given compound under conditions allowing the formation of an phenylthiazole ligand 1-PI3K complex, and
c) detecting the phenylthiazole ligand 1-PI3K complex formed in step b).

In a third aspect, the invention provides a method for the identification of a PI3K interacting compound, comprising the steps of:
a) providing two aliquots of a protein preparation containing PI3K,
b) contacting one aliquot with phenylthiazole ligand 1 immobilized on a solid support under conditions allowing the formation of an phenylthiazole ligand 1-PI3K complex,
c) contacting the other aliquot with phenylthiazole ligand 1 immobilized on a solid support and with a given compound under conditions allowing the formation of an phenylthiazole ligand 1-PI3K complex, and
d) determining the amount of phenylthiazole ligand 1-PI3K complex formed in steps b) and c).

In a fourth aspect, the invention relates to a method for the identification of a PI3K interacting compound, comprising the steps of:
a) providing two aliquots comprising each at least one cell containing PI3K,
b) incubating one aliquot with a given compound,
c) harvesting the cells of each aliquot,
d) lysing the cells in order to obtain protein preparations,
e) contacting the protein preparations with phenylthiazole ligand 1 immobilized on a solid support under conditions allowing the formation of an phenylthiazole ligand 1-PI3K complex, and
f) determining the amount of phenylthiazole ligand 1-PI3K complex formed in each aliquot in step e).

In the context of the present invention, it has been surprisingly found that phenylthiazole ligand 1 is a PI3K ligand. This enables the use of phenylthiazole ligand 1 in screening assays, e.g. in competitive screening assays as well as in methods for the purification of PI3K.

The structure of phenylthiazole ligand 1 is given in FIG. 1. This compound is a substituted thiazole (3-(2-{2-[2-(2-amino-ethoxy)-ethoxy]-ethoxy}-ethoxy)-N-[5-(4-chloro-3-methanesulfonyl-phenyl)-4-methyl-thiazol-2yl]-propionamide) which according to FIG. 1 has hydrochloride as the anion in liquid solution. However, further counter ions are also envisaged in the context of the present invention. The phenylthiazole ligand 1 can be covalently coupled to a suitable solid support material via the primary amino group and be used for the isolation of binding proteins. The synthesis of phenylthiazole ligand 1 is described in Example 1. According to the invention, the expression "phenylthiazole ligand 1" also includes compounds comprising the identical core but which have another linker, preferably coupled to the nitrogen not being part of the cyclic structures, for linkage to the solid support. Typically linkers have backbone of 8, 9 or 10 atoms. The linkers may contain either a carboxy-, hydroxy or amino-active group.

Therefore, in a preferred embodiment, the expression "phenylthiazole ligand 1" also includes compounds having the same N-[5-(4-chloro-3-methanesulfonyl-phenyl)-4-methyl-thiazol-2yl]-propionamide core but comprise another linker at the N-atom, e.g. a C1-C8 alkylcarbonyl or a C1-C8 alkylaminocarbonyl, either of which being optionally substituted by halogen, hydroxy, amino, C1-C8-alkylamino, C1-C8-alkoxycarbonyl, C1-C8-alkoxy optionally substituted by hydroxyl or C1-C8-alkyl optionally substituted by hydroxyl or halogen. Furthermore, this expression also includes compounds as described above which have instead of the 4-chloro residue another halogen, e.g. bromide or which are further substituted at the phenyl ring, e.g. by halogen. Furthermore, instead of the methane sulfonyl group, also another group like a hydroxyl, carboxyl or C1-C8 alkyl group, optionally substituted by halogen, may be present.

In an especially preferred embodiment, compounds falling under the expression "phenylthiazole ligand 1" are selected from the group consisting of 3-(2-{2-[2-(2-amino-ethoxy)-ethoxy]-ethoxy}-ethoxy-N-[5-(4-chloro-3-methanesulfonyl-phenyl)-4-methyl-thiazol-2yl]-propionamide hydrochloride, 3-(2-{2-[2-(2-amino-ethoxy)-ethoxy]-ethoxy}-ethoxy)-N-[5-(4-chloro-3-methanesulfonyl-phenyl)-4-methyl-thiazol-2yl]-propionamide, and compounds with the same N-[5-(4-chloro-3-methanesulfonyl-phenyl)-4-methyl-thiazol-2yl]-propionamide core which are only further substituted at the N-atom by C1-C8 alkylcarbonyl or C1-C8 alkylaminocarbonyl, either of which being optionally substituted by halogen, hydroxy, amino, C1-C8-alkylamino, C1-C8-alkoxycarbonyl, C1-C8-alkoxy optionally substituted by hydroxyl or C1-C8-alkyl optionally substituted by hydroxyl or halogen According to the present invention "PI3K" comprises all members of the PI3K family comprising class IA (e.g. PI3K alpha, beta and delta), class IB (e.g. PI3K gamma), class II (e.g. PI3KC2 alpha, beta and gamma) and class III (e.g. Vps34 yeast homologue).

The sequence of human PI3K gamma (the so far only known member of class IB) is given in FIG. 4.

The sequence of human PI3K delta (a member of class IA) is given in FIG. 5.

According to the present invention, the expression "PI3K" relates to both human and other proteins of this family. The expression especially includes functionally active derivatives thereof, or functionally active fragments thereof, or a homologues thereof, or variants encoded by a nucleic acid that hybridizes to the nucleic acid encoding said protein under low stringency conditions. Preferably, these low stringency conditions include hybridization in a buffer comprising 35% formamide, 5×SSC, 50 mM Tris-HCl (pH 7.5), 5 mM EDTA, 0.02% PVP, 0.02% BSA, 100 ug/ml denatured salmon sperm DNA, and 10% (wt/vol) dextran sulfate for 18-20 hours at 40° C., washing in a buffer consisting of 2×SSC, 25 mM Tris-HCl (pH 7.4), 5 mM EDTA, and 0.1% SDS for 1-5 hours at 55° C., and washing in a buffer consisting of 2×SSC, 25 mM Tris-HCl (pH 7.4) 5 mM EDTA, and 0.1% SDS for 1.5 hours at 60° C.

Phenylthiazole ligand 1 is a ligand for all isoforms of PI3K (see above). However, throughout the invention, it is preferred that PI3K is PI3K gamma or PI3K delta, especially the human isoforms thereof.

In some aspects of the invention, first a protein preparation containing PI3K is provided. The methods of the present invention can be performed with any protein preparation as a starting material, as long as the PI3K is solubilized in the preparation. Examples include a liquid mixture of several proteins, a cell lysate, a partial cell lysate which contains not all proteins present in the original cell or a combination of several cell lysates. The term "protein preparation" also includes dissolved purified protein.

The presence of PI3K protein species in a protein preparation of interest can be detected on Western blots probed with antibodies that are specifically directed against PI3K. In case that PI3K is a specific isoform (e.g. PIK3 gamma and/or PI3K delta), the presence of said isoform can be determined by an isoform-specific antibody. Such antibodies are known in the art (Sasaki et al., 2000, Nature 406, 897-902; Deora et al., 1998, J. Biol. Chem. 273, 29923-29928). Alternatively, also mass spectrometry (MS) could be used (see below).

Cell lysates or partial cell lysates can be obtained by isolating cell organelles (e.g. nucleus, mitochondria, ribosomes, golgi etc.) first and then preparing protein preparations derived from these organelles. Methods for the isolation of cell organelles are known in the art (Chapter 4.2 Purification of Organelles from Mammalian Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

In addition, protein preparations can be prepared by fractionation of cell extracts thereby enriching specific types of proteins such as cytoplasmic or membrane proteins (Chapter 4.3 Subcellular Fractionation of Tissue Culture Cells in "Current Protocols in Protein Science", Editors: John. E. Coligan, Ben M. Dunn, Hidde L. Ploegh, David W. Speicher, Paul T. Wingfield; Wiley, ISBN: 0-471-14098-8).

Furthermore protein preparations from body fluids can be used (e.g. blood, cerebrospinal fluid, peritoneal fluid and urine).

For example whole embryo lysates derived from defined development stages or adult stages of model organisms such as C. elegans can be used. In addition, whole organs such as heart dissected from mice can be the source of protein preparations. These organs can also be perfused in vitro in order to obtain a protein preparation.

Furthermore, the protein preparation may be a preparation containing PI3K which has been recombinantly produced. Methods for the production of recombinant proteins in prokaryotic and eukaryotic cells are widely established (Chapter 5 Production of Recombinant Proteins in "Current Protocols in Protein Science", Editors: John. E. Coligan, Ben M. Dunn, Hidde L. Ploegh, David W. Speicher, Paul T. Wingfield; Wiley, 1995, ISBN: 0-471-14098-8).

In a preferred embodiment of the methods of the invention, the provision of a protein preparation includes the steps of harvesting at least one cell containing PI3K and lysing the cell.

Suitable cells for this purpose are e.g. those cells or tissues were members of the PIK3 family are expressed. Members of the PI3K family are expressed in most cells and tissues. PI3K gamma is preferentially expressed in cells of the hematopoietic system (e.g. granulocytes, macrophages, mast cells and platelets) but also in cardiomyocytes, vascular smooth muscle and vascular epithelium cells. PI3K delta is ubiquitously expressed with pronounced expression in lymphocytes, granulocytes and mast cells.

Therefore, in a preferred embodiment, cells isolated from peripheral blood represent a suitable biological material. Procedures for the preparation and culture of human lymphocytes and lymphocyte subpopulations obtained from peripheral blood (PBLs) are widely known (W. E Biddison, Chapter 2.2 "Preparation and culture of human lymphocytes" in Current Protocols in Cell Biology, 1998, John Wiley & Sons, Inc.). For example, density gradient centrifugation is a method for the separation of lymphocytes from other blood cell populations (e.g. erythrocytes and granulocytes). Human lymphocyte subpopulations can be isolated via their specific cell surface receptors which can be recognized by monoclonal antibodies. The physical separation method involves coupling of these antibody reagents to magnetic beads which allow the enrichment of cells that are bound by these antibodies (positive selection). The isolated lymphocyte cells can be further cultured and stimulated by adding antibodies directed against the T-cell receptor or co-receptors such as CD-3 to initiate T-cell receptor signaling and subsequently phosphorylation of PI3K (Houtman et al., 2005, The Journal of Immunology 175(4), 2449-2458).

As an alternative to primary human cells cultured cell lines (e.g. MOLT-4 cells or rat basophilic leukemia (RBL-2H3) cells) can be used. RBL-2H3 cells can be stimulated by crosslinking the high-affinity receptor for IgE (FcepsilonRI) by multivalent antigens to induce activation of PI3K (Kato et al., 2006, J. Immunol. 177(1): 147-154).

In a preferred embodiment, the cell is part of a cell culture system and methods for the harvest of a cell out of a cell culture system are known in the art (literature supra).

The choice of the cell will mainly depend on the expression of PI3K, since it has to be ensured that the protein is principally present in the cell of choice. In order to determine whether a given cell is a suitable starting system for the methods of the invention, methods like Westernblot, PCR-based nucleic acids detection methods, Northernblots and DNA-microarray methods ("DNA chips") might be suitable in order to determine whether a given protein of interest is present in the cell.

The choice of the cell may also be influenced by the purpose of the study. If the in vivo efficacy for a given drug needs to be analyze then cells or tissues may be selected in which the desired therapeutic effect occurs (e.g. granulocytes or mast cells). By contrast, for the elucidation of protein targets mediating unwanted side effects the cell or tissue may be analysed in which the side effect is observed (e.g. cardiomyocytes, vascular smooth muscle or epithelium cells).

Furthermore, it is envisaged within the present invention that the cell containing PI3K may be obtained from an organism, e.g. by biopsy. Corresponding methods are known in the art. For example, a biopsy is a diagnostic procedure used to obtain a small amount of tissue, which can then be examined microscopically or with biochemical methods. Biopsies are important to diagnose, classify and stage a disease, but also to evaluate and monitor drug treatment.

It is encompassed within the present invention that by the harvest of the at least one cell, the lysis is performed simultaneously. However, it is equally preferred that the cell is first harvested and then separately lysed.

Methods for the lysis of cells are known in the art (Karwa and Mitra: Sample preparation for the extraction, isolation, and purification of Nuclei Acids; chapter 8 in "Sample Preparation Techniques in Analytical Chemistry", Wiley 2003, Editor: Somenath Mitra, print ISBN: 0471328456; online ISBN: 0471457817). Lysis of different cell types and tissues can be achieved by homogenizers (e.g. Potter-homogenizer), ultrasonic disintegrators, enzymatic lysis, detergents (e.g. NP-40, Triton X-100, CHAPS, SDS), osmotic shock, repeated freezing and thawing, or a combination of these methods.

According to the methods of the invention, the protein preparation containing PI3K is contacted with the phenylthiazole ligand 1 immobilized on a solid support under conditions allowing the formation of a phenylthiazole ligand 1-PI3K complex.

In the present invention, the term "a phenylthiazole ligand 1-PI3K complex" denotes a complex where phenylthiazole ligand 1 interacts with PI3K, e.g. by covalent or, most preferred, by non-covalent binding.

The skilled person will know which conditions can be applied in order to enable the formation of the phenylthiazole ligand 1-PI3K complex.

In the context of the present invention, the term "under conditions allowing the formation of the complex" includes all conditions under which such formation, preferably such binding is possible. This includes the possibility of having the solid support on an immobilized phase and pouring the lysate onto it. In another preferred embodiment, it is also included that the solid support is in a particulate form and mixed with the cell lysate.

In the context of non-covalent binding, the binding between phenylthiazole ligand 1 and PI3K is, e.g., via salt bridges, hydrogen bonds, hydrophobic interactions or a combination thereof.

In a preferred embodiment, the steps of the formation of the phenylthiazole ligand 1-PI3K complex are performed under essentially physiological conditions. The physical state of proteins within cells is described in Petty, 1998 (Howard R. Petty[1], Chapter 1, Unit 1.5 in: Juan S. Bonifacino, Mary Dasso, Joe B. Harford, Jennifer Lippincott-Schwartz, and Kenneth M. Yamada (eds.) *Current Protocols in Cell Biology* Copyright © 2003 John Wiley & Sons, Inc. All rights reserved. DOI: 10.1002/0471143030.cb0101s00Online Posting Date: May, 2001Print Publication Date: October, 1998).

The contacting under essentially physiological conditions has the advantage that the interactions between the ligand, the cell preparation (i.e. the kinase to be characterized) and optionally the compound reflect as much as possible the natural conditions. "Essentially physiological conditions" are inter alia those conditions which are present in the original, unprocessed sample material. They include the physiological protein concentration, pH, salt concentration, buffer capacity and post-translational modifications of the proteins involved. The term "essentially physiological conditions" does not require conditions identical to those in the original living organism, wherefrom the sample is derived, but essentially cell-like conditions or conditions close to cellular conditions. The person skilled in the art will, of course, realize that certain constraints may arise due to the experimental set-up which will eventually lead to less cell-like conditions. For example, the eventually necessary disruption of cell walls or cell membranes when taking and processing a sample from a living organism may require conditions which are not identical to the physiological conditions found in the organism. Suitable variations of physiological conditions for practicing the methods of the invention will be apparent to those skilled in the art and are encompassed by the term "essentially physiological conditions" as used herein. In summary, it is to be understood that the term "essentially physiological conditions" relates to conditions close to physiological conditions, as e.g. found in natural cells, but does not necessarily require that these conditions are identical.

For example, "essentially physiological conditions" may comprise 50-200 mM NaCl or KCl, pH 6.5-8.5, 20-37° C., and 0.001-10 mM divalent cation (e.g. Mg++, Ca++,); more preferably about 150 m NaCl or KCl, pH7.2 to 7.6, 5 mM divalent cation and often include 0.01-1.0 percent non-specific protein (e.g. BSA). A non-ionic detergent (Tween, NP-40, Triton-X100) can often be present, usually at about 0.001 to 2%, typically 0.05-0.2% (volume/volume). For general guidance, the following buffered aqeuous conditions may be applicable: 10-250 mM NaCl, 5-50 mM Tris HCl, pH5-8, with optional addition of divalent cation(s) and/or metal chelators and/or non-ionic detergents.

Preferably, "essentially physiological conditions" mean a pH of from 6.5 to 7.5, preferably from 7.0 to 7.5, and/or a buffer concentration of from 10 to 50 mM, preferably from 25 to 50 mM, and/or a concentration of monovalent salts (e.g. Na or K) of from 120 to 170 mM, preferably 150 mM. Divalent salts (e.g. Mg or Ca) may further be present at a concentration of from 1 to 5 mM, preferably 1 to 2 mM, wherein more preferably the buffer is selected from the group consisting of Tris-HCl or HEPES.

In the context of the present invention, phenylthiazole ligand 1 is immobilized on a solid support. Throughout the invention, the term "solid support" relates to every undissolved support being able to immobilize a small molecule ligand on its surface.

According to a further preferred embodiment, the solid support is selected from the group consisting of agarose, modified agarose, sepharose beads (e.g. NHS-activated sepharose), latex, cellulose, and ferro- or ferrimagnetic particles.

Phenylthiazole ligand 1 may be coupled to the solid support either covalently or non-covalently. Non-covalent binding includes binding via biotin affinity ligands binding to streptavidin matrices.

Preferably, the phenylthiazole ligand 1 is covalently coupled to the solid support.

Before the coupling, the matrixes can contain active groups such as NHS, Carbodimide etc. to enable the coupling reaction with the phenylthiazole ligand 1. The phenylthiazole ligand 1 can be coupled to the solid support by direct coupling (e.g. using functional groups such as amino-, sulfhydryl-, carboxyl-, hydroxyl-, aldehyde-, and ketone groups) and by indirect coupling (e.g. via biotin, biotin being covalently attached to phenylthiazole ligand 1 and non-covalent binding of biotin to streptavidin which is bound to solid support directly).

The linkage to the solid support material may involve cleavable and non-cleavable linkers. The cleavage may be achieved by enzymatic cleavage or treatment with suitable chemical methods.

Preferred binding interfaces for binding phenylthiazole ligand 1 to solid support material are linkers with a C-atom backbone. Typically linkers have backbone of 8, 9 or 10 atoms. The linkers contain either a carboxy- or amino-active group.

The skilled person will appreciate that between the individual steps of the methods of the invention, washing steps may be necessary. Such washing is part of the knowledge of the person skilled in the art. The washing serves to remove non-bound components of the cell lysate from the solid support. Nonspecific (e.g. simple ionic) binding interactions can be minimized by adding low levels of detergent or by moderate adjustments to salt concentrations in the wash buffer.

According to the identification methods of the invention, the read-out system is either the detection or determination of PI3K (first aspect of the invention), the detection of the phenylthiazole ligand 1-PI3K complex (second aspect of the invention), or the determination of the amount of the phenylthiazole ligand 1-PI3K complex (second, third and forth aspect of the invention).

In the method according to the first aspect of the invention, the detection or determination of separated PI3K is preferably indicative for the fact that the compound is able to separate PI3K from the immobilized phenylthiazole ligand 1. This capacity indicates that the respective compound interacts, preferably binds to PI3K, which is indicative for its therapeutic potential.

In one embodiment of the method according to the second aspect of the invention, the phenylthiazole ligand 1-PI3K complex formed during the method of the invention is detected. The fact that such complex is formed preferably indicates that the compound does not completely inhibit the formation of the complex. On the other hand, if no complex is formed, the compound is presumably a strong interactor with PI3K, which is indicative for its therapeutic potential.

According to the methods of the second, third and forth aspect of the invention the amount of the phenylthiazole ligand 1-PI3K complex formed during the method is determined. In general, the less complex in the presence of the respective compound is formed, the stronger the respective compound interacts with PI3K, which is indicative for its therapeutic potential.

The detection of the phenylthiazole ligand 1-PI3K complex according to the second aspect of the invention can be performed by using labeled antibodies directed against PI3K and a suitable readout system.

According to a preferred embodiment of the second aspect of the invention, the phenylthiazole ligand 1-PI3K complex is detected by determining its amount.

In the course of the second, third and forth aspect of the invention, it is preferred that PI3K is separated from the immobilized phenylthiazole ligand 1 in order to determine the amount of the phenylthiazole ligand 1-PI3K complex.

According to invention, separating means every action which destroys the interactions between phenylthiazole ligand 1 and PI3K. This includes in a preferred embodiment the elution of PI3K from the immobilized phenylthiazole ligand 1.

The elution can be achieved by using non-specific reagents as described in detail below (ionic strength, pH value, detergents). In addition, it can be tested whether a compound of interest can specifically elute the PI3K from phenylthiazole ligand 1. Such PI3K interacting compounds are described further in the following sections.

Such non-specific methods for destroying the interaction are principally known in the art and depend on the nature of the ligand enzyme interaction. Principally, change of ionic strength, the pH value, the temperature or incubation with detergents are suitable methods to dissociate the target enzymes from the immobilized ligand. The application of an elution buffer can dissociate binding partners by extremes of pH value (high or low pH; e.g. lowering pH by using 0.1 M citrate, pH2-3), change of ionic strength (e.g. high salt concentration using NaI, KI, MgCl2, or KCl), polarity reducing agents which disrupt hydrophobic interactions (e.g. dioxane or ethylene glycol), or denaturing agents (chaotropic salts or detergents such as Sodium-docedyl-sulfate, SDS; Review: Subramanian A., 2002, Immunoaffinty chromatography).

In some cases, the solid support has preferably to be separated from the released material. The individual methods for this depend on the nature of the solid support and are known in the art. If the support material is contained within a column the released material can be collected as column flowthrough. In case the support material is mixed with the lysate components (so called batch procedure) an additional separation step such as gentle centrifugation may be necessary and the released material is collected as supernatant. Alternatively magnetic beads can be used as solid support so that the beads can be eliminated from the sample by using a magnetic device.

In step d) of the method according to the first aspect of the invention, it is determined if PI3K has been separated from the immobilized phenylthiazole ligand 1. This may include the detection of PI3K or the determination of the amount PI3K.

Consequently, at least in preferred embodiments of all identification methods of the invention, methods for the detection of separated PI3K or for the determination of its amount are used. Such methods are known in the art and include physico-chemical methods such as protein sequencing (e.g. Edmann degradation), analysis by mass spectrometry methods or immunodetection methods employing antibodies directed against PI3K.

Throughout the invention, if an antibody is used in order to detect PI3K or in order to determine its amount (e.g. via ELISA), the skilled person will understand that, if a specific isoform of PI3K is to be detected or if the amount of a specific isoform of PI3K is to be determined, an isoform-specific antibody may be used. As indicated above, such antibodies are known in the art. Furthermore, the skilled person is aware of methods for producing the same.

Preferably, PI3K is detected or the amount of PI3K is determined by mass spectrometry or immunodetection methods.

The identification of proteins with mass spectrometric analysis (mass spectrometry) is known in the art (Shevchenko et al., 1996, Analytical Chemistry 68: 850-858; Mann et al., 2001, Analysis of proteins and proteomes by mass spectrometry, Annual Review of Biochemistry 70, 437-473) and is further illustrated in the example section.

Preferably, the mass spectrometry analysis is performed in a quantitative manner, for example by using iTRAQ technology (isobaric tags for relative and absolute quantification) or cICAT (cleavable isotope-coded affinity tags) (Wu et al., 2006. J. Proteome Res. 5, 651-658).

According to a further preferred embodiment of the present invention, the characterization by mass spectrometry (MS) is performed by the identification of proteotypic peptides of PI3K. The idea is that PI3K is digested with proteases and the resulting peptides are determined by MS. As a result, peptide frequencies for peptides from the same source protein differ by a great degree, the most frequently observed peptides that "typically" contribute to the identification of this protein being termed "proteotypic peptide". Therefore, a proteotypic peptide as used in the present invention is an experimentally well observable peptide that uniquely identifies a specific protein or protein isoform.

According to a preferred embodiment, the characterization is performed by comparing the proteotypic peptides obtained in the course of practicing the methods of the invention with known proteotypic peptides. Since, when using fragments prepared by protease digestion for the identification of a protein in MS, usually the same proteotypic peptides are observed for a given enzyme, it is possible to compare the proteotypic peptides obtained for a given sample with the proteotypic peptides already known for enzymes of a given class of enzymes and thereby identifying the enzyme being present in the sample.

As an alternative to mass spectrometry analysis, the eluted PI3K (including coeluted binding partners or scaffold proteins), can be detected or its amount can be determined by using a specific antibody directed against PI3K (or against an isoform of PI3K, see above).

Furthermore, in another preferred embodiment, once the identity of the coeluted binding partner has been established by mass spectrometry analysis, each binding partner can be detected with specific antibodies directed against this protein.

Suitable antibody-based assays include but are not limited to Western blots, ELISA assays, sandwich ELISA assays and antibody arrays or a combination thereof. The establishment of such assays is known in the art (Chapter 11, Immunology, pages 11-1 to 11-30 in: Short Protocols in Molecular Biology. Fourth Edition, Edited by F. M. Ausubel et al., Wiley, New York, 1999).

These assays can not only be configured in a way to detect and quantify a PI3K interacting protein of interest (e.g. a catalytic or regulatory subunit of a PI3K complex), but also to analyse posttranslational modification patterns such as phosphorylation or ubiquitin modification.

Furthermore, the identification methods of the invention involve the use of compounds which are tested for their ability to be an PI3K interacting compound.

Principally, according to the present invention, such a compound can be every molecule which is able to interact with PI3K, eg. by inhibiting its binding to phenylthiazole ligand 1. Preferably, the compound has an effect on PI3K, e.g. a stimulatory or inhibitory effect.

Preferably, said compound is selected from the group consisting of synthetic or naturally occurring chemical compounds or organic synthetic drugs, more preferably small molecules, organic drugs or natural small molecule compounds. Preferably, said compound is identified starting from a library containing such compounds. Then, in the course of the present invention, such a library is screened.

Such small molecules are preferably not proteins or nucleic acids. Preferably, small molecules exhibit a molecular weight of less than 1000 Da, more preferred less than 750 Da, most preferred less than 500 Da.

A "library" according to the present invention relates to a (mostly large) collection of (numerous) different chemical entities that are provided in a sorted manner that enables both a fast functional analysis (screening) of the different individual entities, and at the same time provide for a rapid identification of the individual entities that form the library. Examples are collections of tubes or wells or spots on surfaces that contain chemical compounds that can be added into reactions with one or more defined potentially interacting partners in a high-throughput fashion. After the identification of a desired "positive" interaction of both partners, the respective compound can be rapidly identified due to the library construction. Libraries of synthetic and natural origins can either be purchased or designed by the skilled artisan.

Examples of the construction of libraries are provided in, for example, Breinbauer R, Manger M, Scheck M, Waldmann H. Natural product guided compound library development. Curr Med Chem. 2002 December; 9(23):2129-45, wherein natural products are described that are biologically validated starting points for the design of combinatorial libraries, as they have a proven record of biological relevance. This special role of natural products in medicinal chemistry and chemical biology can be interpreted in the light of new insights about the domain architecture of proteins gained by structural biology and bioinformatics. In order to fulfill the specific requirements of the individual binding pocket within a domain family it may be necessary to optimise the natural product structure by chemical variation. Solid-phase chemistry is said to become an efficient tool for this optimisation process, and recent advances in this field are highlighted in this review article. Other related references include Edwards P J, Morrell A I. Solid-phase compound library synthesis in drug design and development. Curr Opin Drug Discov Devel. 2002 July; 5(4):594-605; Merlot C, Domine D, Church D J. Fragment analysis in small molecule discovery. Curr Opin Drug Discov Devel. 2002 May; 5(3):391-9. Review; Goodnow R A Jr. Current practices in generation of small molecule new leads. J Cell Biochem Suppl. 2001; Suppl 37:13-21; which describes that the current drug discovery processes in many pharmaceutical companies require large and growing collections of high quality lead structures for use in high throughput screening assays. Collections of small molecules with diverse structures and "drug-like" properties have, in the past, been acquired by several means: by archive of previous internal lead optimisation efforts, by purchase from compound vendors, and by union of separate collections following company mergers. Although high throughput/combinatorial chemistry is described as being an important component in the process of new lead generation, the selection of library designs for synthesis and the subsequent design of library members has evolved to a new level of challenge and importance. The potential benefits of screening multiple small molecule compound library designs against multiple biological targets offers substantial opportunity to discover new lead structures.

In a preferred embodiment of the second and third aspect of the invention, the PI3K containing protein preparation is first incubated with the compound and then with the immobilized phenylthiazole ligand 1. However, the simultaneous incubation of the compound and the immobilized phenylthiazole ligand 1 (coincubation) with the PI3K containing protein preparation is equally preferred (competitive binding assay).

In case that the incubation with the compound is first, the PI3K is preferably first incubated with the compound for 10 to 60 minutes, more preferred 30 to 45 minutes at a temperature of 4° C. to 37° C., more preferred 4° C. to 25° C., most preferred 4° C. Preferably compounds are used at concentrations ranging from 1 µM to 1 mM, preferably from 10 to 100 µM. The second step, contacting with the immobilized ligand, is preferably performed for 10 to 60 minutes at 4° C.

In case of simultaneous incubation, the PI3K is preferably simultaneously incubated with the compound and phenylthiazole ligand 1 for 30 to 120 minutes, more preferred 60 to 120 minutes at a temperature of 4° C. to 37° C., more preferred 4° C. to 25° C., most preferred 4° C. Preferably compounds are used at concentrations ranging from 1 µM to 1 mM, preferably from 10 to 100 µM.

Furthermore, steps a) to c) of the second aspect of the invention may be performed with several protein preparations in order to test different compounds. This embodiment is especially interesting in the context of medium or high throughput screenings (see below).

In a preferred embodiment of the method of the invention according to the third or forth aspect, the amount of the phenylthiazole ligand 1-PI3K complex formed in step c) is compared to the amount formed in step b)

In a preferred embodiment of the method of the invention according to the third or forth aspect, a reduced amount of the phenylthiazole ligand 1-PI3K complex formed in step c) in comparison to step b) indicates that PI3K is a target of the compound. This results from the fact that in step c) of this method of the invention, the compound competes with the ligand for the binding of PI3K. If less PI3K is present in the aliquot incubated with the compound, this means preferably that the compound has competed with the inhibitor for the interaction with the enzyme and is, therefore, a direct target of the protein and vice versa.

Preferably, the identification methods of the invention are performed as a medium or high throughput screening.

The interaction compound identified according to the present invention may be further characterized by determining whether it has an effect on PI3K, for example on its kinase activity (Carpenter et al., 1990, J. Biol. Chem. 265, 19704-19711). Such assays are known in the art, also in a format that allows medium to high throughput screening (Fuchikami et al., 2002, J. Biomol. Screening 7, 441-450).

Briefly, PI3K lipid kinase activity can be measured using solution-based assays with phospholipid vesicles. The reaction is terminated by the addition of acidified organic solvents and subsequent phase separation by extraction or thin layer chromatography analysis (Carpenter et al., 1990, J. Biol. Chem. 265, 19704-19711).

Alternatively, a fluorescence polarization assay format can be used. Briefly, PI3K is incubated with a suitable phosphoinositol substrate. After the reaction is complete the reaction products are mixed with a specific phosphoinositol detector protein and a fluorescent phosphoinositol probe. The polarization (mP) values decrease as probe binding to the phosphoinositol detector protein is displaced by the reaction product. The degree of polarization of the fluorescent probe is inversely proportional to the amount of the product of the PI3K reaction (Drees et al., 2003, Comb. Chem. High Throughput Screening 6, 321-330).

For the determination of PI3K protein kinase activity a fluorescence polarization assay with a suitable peptide substrate can be used. Briefly, a fluorescein-labeled peptide substrate may be incubated with PI3K (e.g. PI3K delta), ATP and an anti-phosphoserine antibody. As the reaction proceeds, the phosphorylated peptide binds to the anti-phosphoserine antibody, resulting in an increase in the polarization signal. Compounds that inhibit the kinase result in a low polarization signal.

The compounds identified according to the present invention may further be optimized (lead optimisation). This subsequent optimisation of such compounds is often accelerated because of the structure-activity relationship (SAR) information encoded in these lead generation libraries. Lead optimisation is often facilitated due to the ready applicability of high-throughput chemistry (HTC) methods for follow-up synthesis.

One example of such a library and lead optimization is described for PI3K gamma (Pomel et al., 2006, J. med. Chem. 49, 3857-3871).

The invention further relates to a method for the preparation of a pharmaceutical composition comprising the steps of
   a) identifying a PI3K interacting compound as described above, and
   b) formulating the interacting compound to a pharmaceutical composition.

Therefore, the invention provides a method for the preparation of pharmaceutical compositions, which may be administered to a subject in an effective amount. In a preferred aspect, the therapeutic is substantially purified. The subject to be treated is preferably an animal including, but not limited to animals such as cows, pigs, horses, chickens, cats, dogs, etc., and is preferably a mammal, and most preferably human. In a specific embodiment, a non-human mammal is the subject.

The compounds identified according to the invention are useful for the prevention or treatment of diseases where PI3K plays a role such as cancer (e.g. breast, colon or ovary cancer), metabolic disorders (e.g. diabetes or obesity) or autoimmune/inflammatory disorders (e.g. rheumatic arthritis, psoriasis, Crohn's disease, ulcerative colitis, asthma or allergic reactions)

Consequently, the present invention also relates to the use of a compound identified by the methods of the invention for the preparation of a medicament for the treatment of one or more of the above mentioned diseases. Furthermore, the present invention relates to a pharmaceutical composition comprising said compound.

In general, the pharmaceutical compositions of the present invention comprise a therapeutically effective amount of a therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

The therapeutics of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and ferric hydroxides, etc.

The amount of the therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems. In general, suppositories may contain active ingredient in the range of 0.5% to 10% by weight; oral formulations preferably contain 10% to 95% active ingredient.

Various delivery systems are known and can be used to administer a therapeutic of the invention, e.g., encapsulation in liposomes, microparticles, and microcapsules: use of recombinant cells capable of expressing the therapeutic, use of receptor-mediated endocytosis (e.g., Wu and Wu, 1987, J. Biol. Chem. 262:4429-4432); construction of a therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, the therapeutic can be delivered in a vesicle, in particular a liposome (Langer, 1990, Science 249:1527-1533).

In yet another embodiment, the therapeutic can be delivered via a controlled release system. In one embodiment, a pump may be used (Langer, supra). In yet another embodiment, a controlled release system can be placed in proximity of the therapeutic target, i.e., the brain, thus requiring only a fraction of the systemic dose The invention further relates to a method for the purification of PI3K, comprising the steps of
 a) providing a protein preparation containing PI3K,
 b) contacting the protein preparation with phenylthiazole ligand 1 immobilized on a solid support under conditions allowing the formation of an phenylthiazole ligand 1-PI3K complex, and
 c) separating PI3K from the immobilized phenylthiazole ligand 1.

As mentioned above, it has been surprisingly found that phenylthiazole ligand 1 is a ligand which recognizes PI3K. This enables efficient purification methods for PI3K.

With respect to PI3K, the protein preparation containing PI3K, the conditions for contacting with phenylthiazole ligand 1, immobilized phenylthiazole ligand 1, the phenylthiazole ligand 1-PI3K complex, the separation of PI3K from the immobilized phenylthiazole ligand 1, and the detection of PI3K or the determination of its amount, the embodiments as defined above for the identification methods of the invention also apply to the purification method of the invention.

In a preferred embodiment, the method of purification further comprises the step of purifying a specific isoform or specific isoforms of PI3K, preferably the step of purifying PI3K gamma and/or PI3K delta.

Preferably, said purification is performed using an isoform specific antibody as explained above, more preferably a PI3K gamma specific antibody and/or a PI3K delta specific antibody.

In a preferred embodiment, the purification method of the invention further comprises after step c) the identification of proteins being capable of binding to PI3K. This is especially interesting when the formation of the complex is performed under essentially physiological conditions, because it is then possible to preserve the natural condition of the enzyme which includes the existence of binding partners, enzyme subunits or post-translational modifications, which can then be identified with the help of mass spectrometry (MS).

Consequently, in a preferred embodiment, the purification method of the invention further comprises after step c) the determination whether the PI3K is further posttranslationally modified, e.g. by ubiquitine modification.

The invention further relates to the use of phenylthiazole ligand 1 for the identification of PI3K interacting compounds and for the purification of PI3K. The embodiments as defined above also apply to the uses of the invention.

The invention is further illustrated by the following figures and examples, which are not considered as being limiting for the scope of protection conferred by the claims of the present application.

SHORT DESCRIPTION OF THE FIGURES

FIG. 1: Synthesis and Structure of Phenylthiazole Ligand 1.

The phenylthiazole ligand 1 was synthesized as described in example 1.

Figure 2:
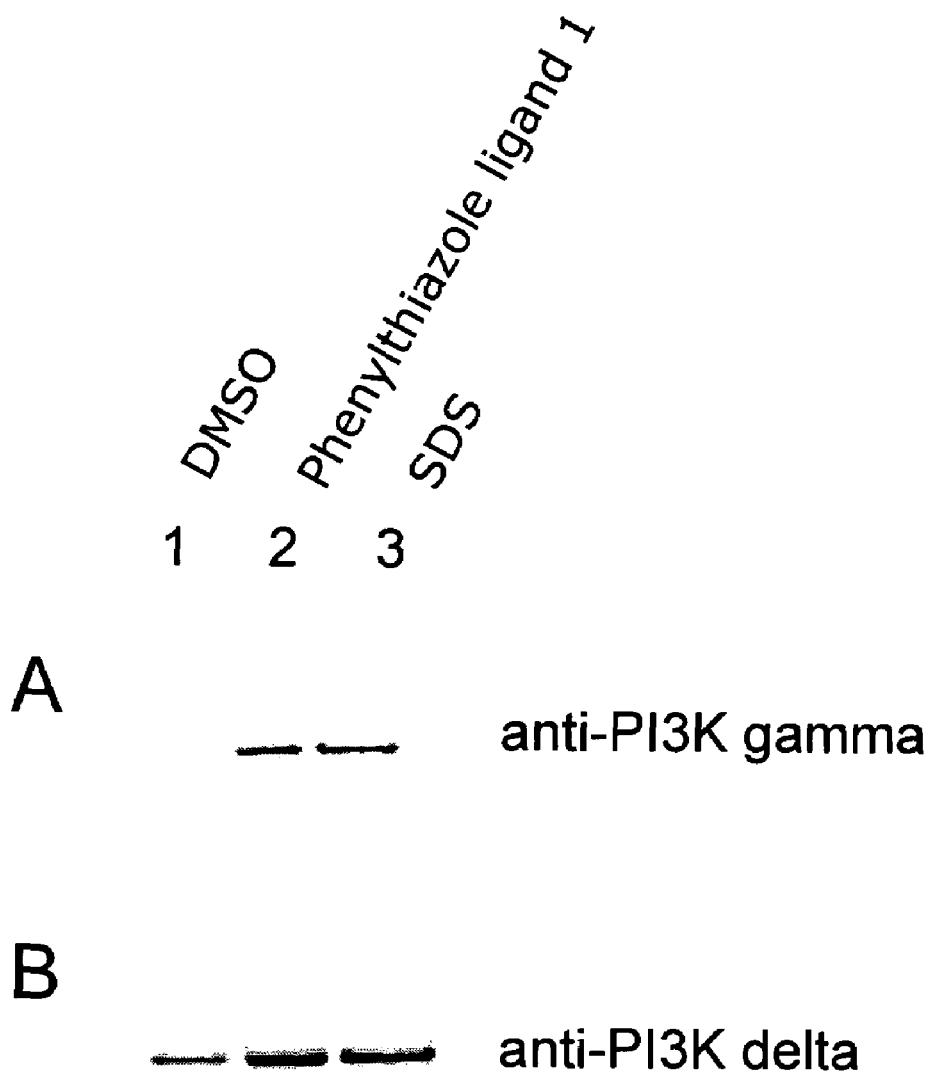

FIG. 2: Drug Pulldown Experiment with Immobilized Phenylthiazole Ligand 1 and Western Blot Detection of PI3K Proteins.

As biological material a cell lysate prepared from MOLT-4 cells was used. The drug pulldown experiment was performed as described in Example 2 with lysate samples containing 50 mg of protein. Captured proteins were eluted with DMSO containing buffer (lane 1), 100 µM of free phenylthiazole ligand 1 or SDS sample buffer (lane 3). The eluted samples were separated on SDS-polyacrylamide gels and transferred to membranes. The blots were first incubated with specific antibodies directed against PI3K gamma (FIG. 2A) and PI3K delta (FIG. 2B). Secondary detection antibodies labeled with fluorescent dyes for detection were used with the Odyssey infrared imaging system.

Lane 1: DMSO elution control; lane 2: elution with 100 µM free phenylthiazole ligand 1; lane 3: SDS elution.

Figure 3:
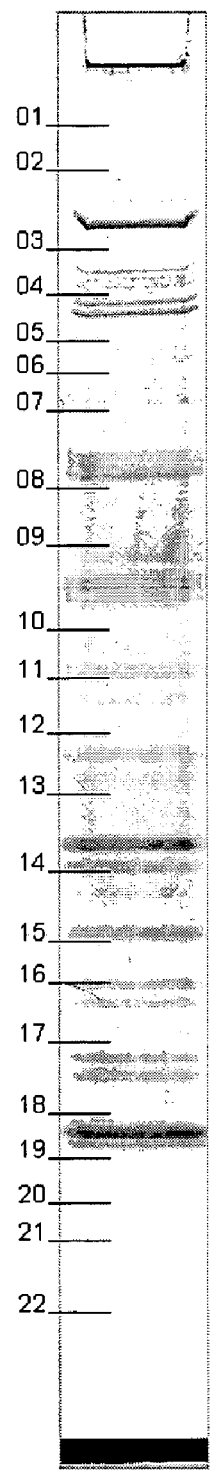

FIG. 3: Drug Pulldown Experiment with Immobilized Phenylthiazole Ligand 1 for Mass Spectrometry Analysis of Proteins.

A protein gel after staining with Coomassie blue is shown. The indicated gel areas were cut out as gel slices and proteins were subjected to analysis by mass spectrometry.

The drug pulldown experiment was performed as described in Example 2 with a MOLT-4 cell lysate sample containing 50 mg of protein. Proteins bound to immobilized phenylthiazole ligand 1 were eluted with SDS sample buffer and separated by SDS-polyacrylamide gel electrophoresis (SDS-PAGE).

FIG. 4: Peptides Identified of PI3K Gamma.

The peptides that were identified by mass spectrometry analysis of the human PI3K delta sequence are shown in bold type and underlined.

FIG. 5: Peptides Identified of PI3K Delta.

The peptides that were identified by mass spectrometry analysis of the human PI3K gamma sequence are shown in bold type and underlined.

Figure 6:
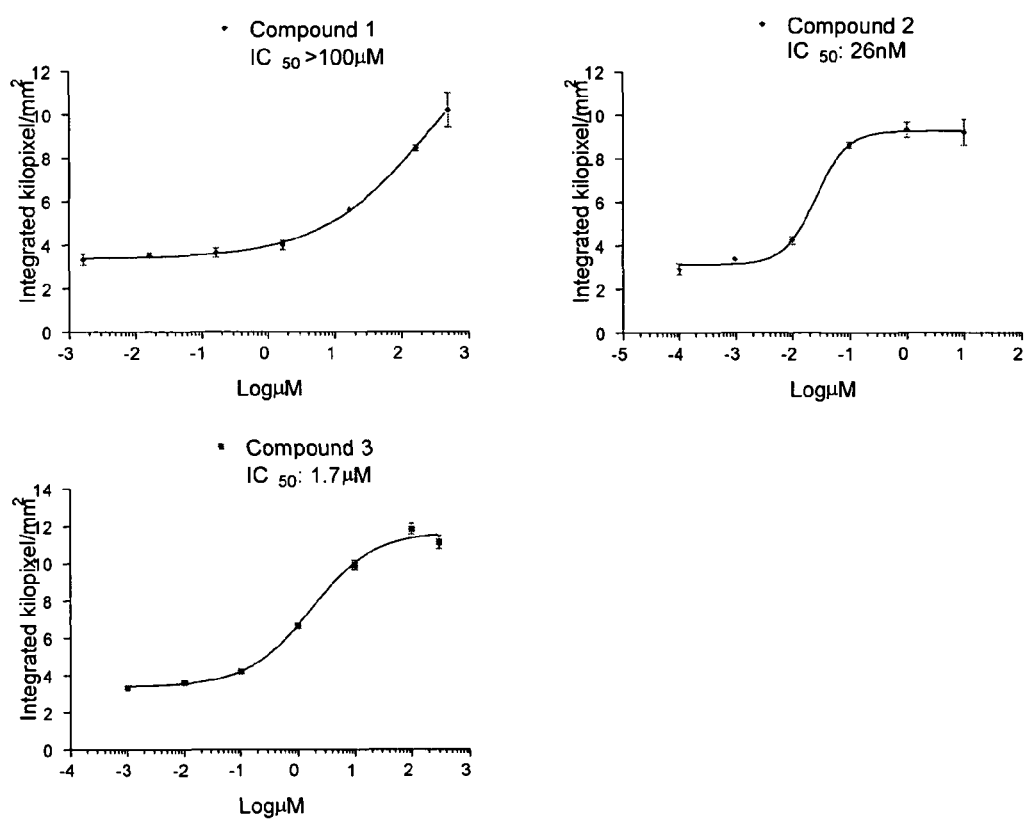

FIG. 6: Elution Assay for the Identification of PI3K Gamma Interacting Compounds.

The experiment was performed as described in example 3. PI3K gamma protein was captured by immobilized phenylthiazole ligand 1 from MOLT-4 cell lysate and eluted by the compounds as indicated. Eluates were transferred to a nitrocellulose membrane and PI3K gamma was detected with the Odyssey Infrared Imaging system. First antibody: anti-PI3K gamma (Jena Bioscience ABD-026S; mouse antibody). Second antibody: anti-mouse IRDye800 (Rockland, 610-732-124). Integrated Intensity (integrated kilopixel/mm$^2$) are shown.

Compounds Used for Elution:
Compound 1 (LY29004); $IC_{50}$>100 µM; compound 2 (AS-605240): $IC_{50}$=26 nM; compound 3 (AS-604850); $IC_{50}$=1.7 µM, FIG. 7: Competitive Binding Assay for the Identification of PI3K Gamma Interacting Compounds.

The experiment was performed as described in example 4. Test compounds at the indicated concentrations and the affinity matrix were added to MOLT-4 cell lysate and the PI3K gamma protein not interacting with test compounds was captured by the immobilized phenylthiazole ligand 1 on the affinity matrix. The affinity matrix was separated from the lysate, bound proteins were eluted with SDS sample buffer and the eluates were transferred to a nitrocellulose membrane. The amount of PI3K gamma was determined with the Odyssey Infrared Imaging system.

7A: Dot blot probed with antibodies and signals detected with Odyssey infrared imaging system. First antibody: anti-PI3K gamma (Jena Bioscience ABD-026S; mouse antibody). Second antibody: anti-mouse IRDye800 (Rockland, 610-732-124).

7B: Competition binding curves. Relative Odyssey units (Integrated Intensity; integrated kilopixel/mm$^2$) are plotted against compound concentrations and half maximal binding competition (IC) values calculated. Compound 1 (LY294002): $IC_{50}$>30 µM; compound 2 (AS-605240): $IC_{50}$=4.6 µM; compound 3 (AS-604850): $IC_{50}$=176 nM.

Figure 8:
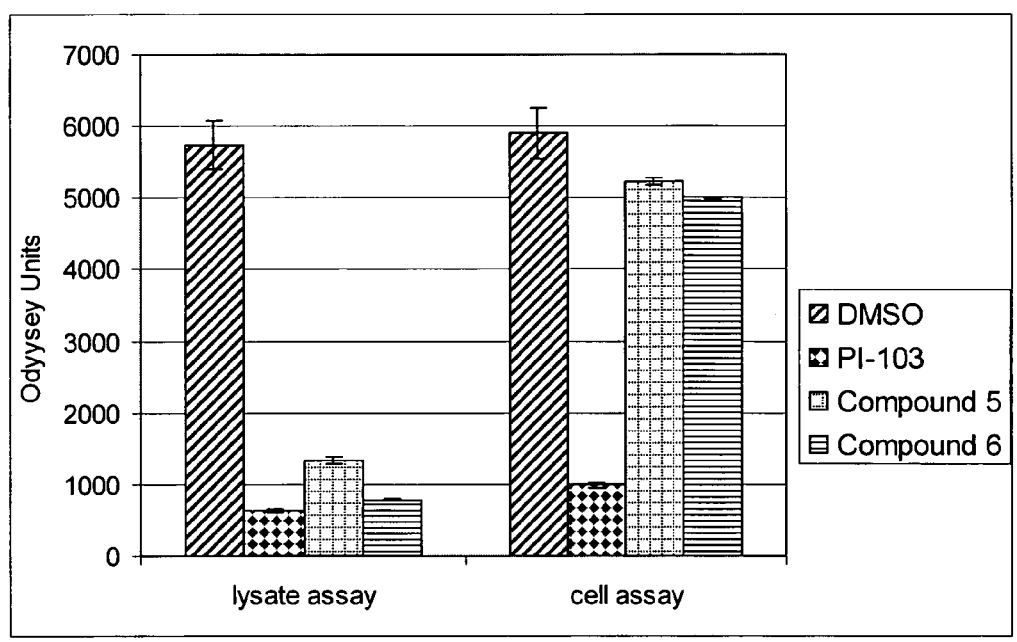

FIG. 8: Compound Profiling by Adding Compounds to Cell Lysates (Lysate Assay) or by Incubating Compound with Living RAW264.7 Cells (Cell Assay).

The experiment was performed as described in example 5. Compounds were used at a concentration of 10 µM in both assays and the amount of PI3Kdelta was quantified with the Odyssey Infrared Imaging system.

EXAMPLE 1

Preparation of the Affinity Matrix

This example illustrates the preparation of the affinity matrix for affinity capture of PI3K kinases from cell lysates. The capturing ligand was covalently immobilized on a solid support through covalent linkage using an amino functional group. This affinity matrix was used in example 2, example 3 and example 4.

Synthesis of phenylthiazole ligand 1 (3-(2-{2-[2-(2-amino-ethoxy)-ethoxy]-ethoxy}-ethoxy)-N-[5-(4-chloro-3-methanesulfonyl-phenyl)-4-methyl-thiazol-2yl]-propionamide hydrochloride)

Steps 1-3: 1-bromo-1-(4-chloro-3-methanesulfonyl-phenyl)-propan-2-one was prepared following the procedure described in WO 2003/072557

Step 4: 5-(4-chloro-3-methanesulfonyl-phenyl)-4-methyl-thiazol-2-ylamine 1-bromo-1-(4-chloro-3-methanesulfonyl-phenyl)-propan-2-one (480 mg 1.5 mmol) and thiourea (114 mg 1.5 mmol) were combined in ethanol (12 ml) and heated to 70° C. for 2 hours. The reaction mixture was allowed to cool to room temperature and the solid product was collected by filtration and dried under vacuum to yield 5-(4-chloro-3-methanesulfonyl-phenyl)-4-methyl-thiazol-2-ylamine as an off-white solid (375 mg). $^1$H NMR (400 MHz DMSO-d$_6$) δ 9.4 (br s, 2H), 8.0 (d, 1H), 7.9 (d, 1H), 7.8 (dd, 1H), 3.4 (s, 3H), 2.3 (s, 3H).

Step 5: (2-{2-[2-(2-{2[5-(4-chloro-3-methanesulfonyl-phenyl)-4-methyl-thiazol-2-ylcarbamoyl]-ethoxy}-ethoxy)-ethoxy]-ethoxy}-ethyl)-carbamic acid tert-butyl ester 3-(2-{2-[2-(2-tert-butoxycarbonylamino-ethoxy)-ethoxy]-ethoxy}-ethoxy)-propionic acid (690 mg 1.9 mmol), EDAC (403 mg 2.1 mmol), HOBT (284 mg 2.1 mmol), NMM (420 uL 3.8 mmol) and 5-(4-chloro-3-methanesulfonyl-phenyl)-4-methyl-thiazol-2-ylamine (520 mg 1.7 mmol) were combined in dimethylformamide (16 ml) and stirred over night at room temperature. The solvent was removed under reduced pressure and the residue dissolved in dichloromethane (150 ml), washed with 1M HCl aqueous solution (50 ml) and saturated aqueous sodium hydrogen carbonate (50 ml), dried (Magnesium sulphate), filtered and evaporated. The residue was purified by flash chromatography using 50 g IST silica flash cartridge eluting with 0-2% methanol/dichloromethane to yield (2-{2-[2-(2-{2[5-(4-chloro-3-methanesulfonyl-phenyl)-4-methyl-thiazol-2-ylcarbamoyl]-ethoxy}-ethoxy)-ethoxy]-ethoxy}-ethyl)-carbamic acid tert-butyl ester as an oil (1.1 g residual solvent present) $^1$H NMR (400 MHz CDCl3) 10.3 (br s, 1H), 8.2 (s, 1H), 7.6 (m, 2H), 7.2 (br s, 1H), 3.9 (t, 2H) 3.8-3.5 (br m, 14H), 3.3 (br m, 5H), 2.8 (t, 2H), 2.4 (s, 3H), 1.4 (s, 9H).

Step 6: 3-(2-{2-[2-(2-amino-ethoxy)-ethoxy]-ethoxy}-ethoxy)-N-[5-(4-chloro-3-methanesulfonyl-phenyl)-4-methyl-thiazol-2yl]-propionamide hydrochloride (2-{2-[2-(2-{2[5-(4-chloro-3-methanesulfonyl-phenyl)-4-methyl-thiazol-2-ylcarbamoyl]-ethoxy}-ethoxy)-ethoxy]-ethoxy}-ethyl)-carbamic acid tert-butyl ester (1.0 g 1.5 mmol) was dissolved in dichloromethane (10 ml) and treated with HCl (4 ml 4M solution in dioxane). The reaction was stirred at room temperature for 3 hours. The solvent was evaporated and the residue dried under vacuum to yield 3-(2-{2-[2-(2-amino-ethoxy)-ethoxy]-ethoxy}-ethoxy)-N-[5-(4- chloro-3-methanesulfonyl-phenyl)-4-methyl-thiazol-2yl]-propionamide hydrochloride as a yellow viscous oil (830 mg residual solvent present) $^1$H NMR (400 MHz CDCl3) 8.4 (br s, 3H), 8.2 (s, 1H), 7.7 (br d, 1H), 7.6 (br d, 1H) 3.9 (br m, 4H), 3.8-3.6 (br m, 12H), 3.3 (s, 3H), 3.3 (br m, 2H), 3.1 (br m, 2H), 2.6 (s, 3H). NMR spectra were obtained on a Bruker dpx400.

TABLE 1

Abbreviations used

| | |
|---|---|
| br | broad |
| CDCl3 | deuterochloroform |
| d | doublet |
| dd | doublet of doublets |
| DMSO | dimethyl sulphoxide |
| EDAC | 1-ethyl-3-(3'-dimethylaminopropyl)carbodiimide |
| g | gram |
| HCl | Hydrochloric acid |
| HOBT | N-Hydroxybenzotriazole |
| m | multiplet |
| mg | milligram |
| ml | millilitre |
| mmol | millimole |
| M | molar |
| MHz | megahertz |
| NMM | N-methyl morpholine |
| NMR | nuclear magnetic resonance |
| q | quartet |
| s | singlet |
| t | triplet |

Immobilization of Phenylthiazole Ligand 1 on Beads (Affinity Matrix)

NHS-activated Sepharose 4 Fast Flow (Amersham Biosciences, 17-0906-01) was equilibrated with anhydrous DMSO (Dimethylsulfoxid, Fluka, 41648, H20<=0.005%). 1 ml of settled beads was placed in a 15 ml Falcon tube, compound stock solution (usually 100 mM in DMF or DMSO) was added (final concentration 0.2-2 µmol/ml beads) as well as 15 µl of triethylamine (Sigma, T-0886, 99% pure). Beads were incubated at room temperature in darkness on an end-over-end shaker (Roto Shake Genie, Scientific Industries Inc.) for 16-20 hours. Coupling efficiency is determined by HPLC. Non-reacted NHS-groups were blocked by incubation with aminoethanol at room temperature on the end-over-end shaker over night. Beads were washed with 10 ml of DMSO and were stored in isopropanol at −20° C. These beads were used as the affinity matrix in example 2, 3 and 4. Control beads (no ligand immobilized) were generated by blocking the NHS-groups by incubation with aminoethanol as described above.

EXAMPLE 2

Drug Pulldown of PI3K Using Immobilized Phenylthiazole Ligand 1

This example demonstrates the use of the immobilized phenylthiazole ligand 1 for the identification of PI3K proteins from cell lysates of a human T cell line (MOLT-4 cells; ATCC number CRL-1582). To this end a lysate of MOLT-4 cells was contacted with the affinity matrix described in example 1. Proteins binding to the phenylthiazole ligand 1 were identified by Western blot and mass spectrometry (MS) analysis.

For Western blot analysis bound proteins were eluted from the affinity matrix and subsequently separated by SDS-Polyacrylamide gel electrophoresis. PI3K gamma and PI3K delta were detected with specific antibodies (FIG. 2). The results of the Western blot analysis show that immobilized phenylthiazole ligand 1 captures (pulls down) PI3K gamma and PI3K delta from the cell lysate.

For the identification of proteins by mass spectrometry analysis the proteins captured by the affinity matrix were eluted and subsequently separated by SDS-Polyacrylamide gel electrophoresis (FIG. 3). Suitable gel bands were cut out and subjected to in-gel proteolytic digestion with trypsin and analyzed by LC-MS/MS mass spectrometry.

The identification of members of the PI3K family is documented in Table 3. The peptide sequence coverage of PI3K gamma is shown in FIG. 4 and for PI3K delta in FIG. 5.

1. Cell Culture

MOLT-4 cells (ATCC number 1582) were grown in 1 liter Spinner flasks (Integra Biosciences, #182101) in suspension in RPMI 1640 medium (Invitrogen, #21875-034) supplemented with 10% Fetal Bovine Serum (Invitrogen) at a density between $0.15 \times 10^6$ and 1.2×10e6 cells/ml. Cells were harvested by centrifugation, washed once with 1×PBS buffer (Invitrogen, #14190-094) and cell pellets were frozen in liquid nitrogen and subsequently stored at −80° C.

2. Preparation of Cell Lysates

MOLT-4 cells were homogenized in a Potter S homogenizer in lysis buffer: 50 mM Tris-HCl, 0.8% NP40, 5% glycerol, 150 mM NaCl, 1.5 mM MgCl2, 25 mM NaF, 1 mM sodium vanadate, 1 mM DTT, pH 7.5. One complete EDTA-free tablet (protease inhibitor cocktail, Roche Diagnostics, 1 873 580) per 25 ml buffer was added. The material was dounced 10 times using a mechanized POTTER S, transferred to 50 ml falcon tubes, incubated for 30 minutes on ice and spun down for 10 min at 20,000 g at 4° C. (10,000 rpm in Sorvall SLA600, precooled). The supernatant was transferred to an ultracentrifuge (UZ)-polycarbonate tube (Beckmann, 355654) and spun for 1 hour at 100.000 g at 4° C. (33.500 rpm in Ti50.2, precooled). The supernatant was transferred again to a fresh 50 ml falcon tube, the protein concentration was determined by a Bradford assay (BioRad) and samples containing 50 mg of protein per aliquot were prepared. The samples were immediately used for experiments or frozen in liquid nitrogen and stored frozen at −80° C.

3. Compound Pull-Down Experiment

Sepharose-beads with immobilized compound (100 µl beads per pull-down experiment) were equilibrated in lysis buffer and incubated with a cell lysate sample containing 50 mg of protein on an end-over-end shaker (Roto Shake Genie, Scientific Industries Inc.) for 2 hours at 4° C. Beads were collected, transferred to Mobicol-columns (MoBiTech 10055) and washed with 10 ml lysis buffer containing 0.5% NP40 detergent, followed by 5 ml lysis buffer with 0.25% detergent. To elute the bound protein, 60 µl 2×SDS sample buffer was added, the column was heated for 30 minutes at 50° C. and the eluate was transferred to a microfuge tube by centrifugation. Proteins were then separated by SDS-Polyacrylamide electrophoresis (SDS-PAGE).

4. Protein Detection by Western Blot Analysis

Western blots were performed according to standard procedures and the PI3K proteins were detected and quantified by using specific anti-PI3K antibodies (first antibody), a fluorescently labeled secondary antibody and the Odyssey Infrared Imaging system from LI-COR Biosciences (Lincoln, Nebr., USA) according to instructions provided by the manufacturer (Schutz-Geschwendener et al., 2004. Quantitative, two-color Western blot detection with infrared fluorescence. Published May 2004 by LI-COR Biosciences, www.licor.com).

The mouse anti PI3K gamma antibody (Jena Bioscience, catalogue number ABD-026S) was used at a dilution of 1:200 and incubated with the blot over night at 4° C. The secondary anti-mouse IRDye™ 800 antibody (Rockland, catalogue number 610-732-124) was used at a dilution of 1:15000. The rabbit anti PI3K delta antibody (Santa Cruz, catalogue number sc-7176 was diluted 1:600 and incubated over night at 4° C. As a secondary detection antibody the anti-rabbit IRDye™ 800 antibody was diluted 1:20 000 (LICOR, catalogue number 926-32211).

5. Protein Identification by Mass Spectrometry 5.1 Protein Digestion Prior to Mass Spectrometric Analysis Gel-separated proteins were reduced, alkylated and digested in gel essentially following the procedure described by Shevchenko et al., 1996, Anal. Chem. 68:850-858. Briefly, gel-separated proteins were excised from the gel using a clean scalpel, reduced using 10 mM DTT (in 5 mM ammonium bicarbonate, 54° C., 45 min) and subsequently alkylated with 55 mM iodoacetamid (in 5 mM ammonium bicarbonate) at room temperature in the dark (30 minutes). Reduced and alkylated proteins were digested in gel with porcine trypsin (Promega) at a protease concentration of 12.5 ng/µl in 5 mM ammonium bicarbonate. Digestion was allowed to proceed for 4 hours at 37° C. and the reaction was subsequently stopped using 5 µl 5% formic acid.

5.2 Sample Preparation Prior to Analysis by Mass Spectrometry

Gel plugs were extracted twice with 20 µl 1% TFA and pooled with acidified digest supernatants. Samples were dried in a vacuum centrifuge and resuspended in 10 µl 0.1% formic acid.

5.3. Mass Spectrometric Data Acquisition

Peptide samples were injected into a nano LC system (CapLC, Waters or Ultimate, Dionex) which was directly coupled either to a quadrupole TOF (QTOF2, QTOF Ultima, QTOF Micro, Micromass) or ion trap (LCQ Deca XP) mass spectrometer. Peptides were separated on the LC system using a gradient of aqueous and organic solvents (see below). Solvent A was 5% acetonitrile in 0.5% formic acid and solvent B was 70% acetonitrile in 0.5% formic acid.

TABLE 2

Peptides eluting off the LC system were partially sequenced within the mass spectrometer.

| Time (min) | % solvent A | % solvent B |
|---|---|---|
| 0 | 95 | 5 |
| 5.33 | 92 | 8 |
| 35 | 50 | 50 |
| 36 | 20 | 80 |
| 40 | 20 | 80 |
| 41 | 95 | 5 |
| 50 | 95 | 5 |

5.4. Protein Identification

The peptide mass and fragmentation data generated in the LC-MS/MS experiments were used to query fasta formatted protein and nucleotide sequence databases maintained and updated regularly at the NCBI (for the NCBInr, dbEST and the human and mouse genomes) and European Bioinformatics Institute (EBI, for the human, mouse, *D. melanogaster* and *C. elegans* proteome databases). Proteins were identified by correlating the measured peptide mass and fragmentation data with the same data computed from the entries in the database using the software tool Mascot (Matrix Science; Perkins et al., 1999. Probability-based protein identification by searching sequence databases using mass spectrometry data. Electrophoresis 20, 3551-3567). Search criteria varied depending on which mass spectrometer was used for the analysis.

TABLE 3

PI3K proteins identified by mass spectrometry (MOLT-4 cells; experiment P15234B; MS sample refers to the gel slice cut out from the polyacrylamide gel (FIG. 3).

| MS sample | Protein accesion number (IPI) | Protein name | Number of peptides identified |
|---|---|---|---|
| 4 | IPI00070943.3 | PIK4CA; phosphatidylinositol 4-kinase, catalytic, alpha polypeptide | 62 |
| 5 | IPI00024006.1 | PIK3R4; phosphoinositide-3-kinase, regulatory subunit 4, p150 | 11 |
| 6 | IPI00292690.1 | PIK3CG; phosphoinositide-3-kinase, catalytic, gamma polypeptide | 39 |
| 6 | IPI00298410.2 | PIK3CD; phosphoinositide-3-kinase, catalytic, delta polypeptide | 26 |
| 7 | IPI00298410.2 | PIK3CD; phosphoinositide-3-kinase, catalytic, delta polypeptide | 12 |
| 8 | IPI00002591.3 | PIK4CB; phosphatidylinositol 4-kinase, catalytic, beta polypeptide | 15 |
| 9 | IPI00021448.1 | PIK3R1; phosphoinositide-3-kinase, regulatory subunit 1 (p85 alpha) | 27 |
| 9 | IPI00011736.3 | PIK3R2; phosphoinositide-3-kinase, regulatory subunit 2 (p85 beta) | 8 |
| 14 | IPI00333040.3 | PIK3R1; phosphoinositide-3-kinase, regulatory subunit 1 (p85 alpha) | 7 |

EXAMPLE 3

Elution Assay for the Identification of PI3K Gamma Interacting Compounds

The preparation of the phenylthiazole ligand 1 affinity matrix was done as described in example 1. To screen maximally 80 compounds in a 96 well plate the elution experiment is performed as described below.

Elution Assay

The affinity matrix (1200 µl of beads) was washed 2× with 30 ml 1×DP-buffer. After each washing step the beads were collected by centrifugation for 2 minutes at 1200 rpm at 4° C. in a Heraeus centrifuge. The supernatants were discarded. Finally, the beads were equilibrated in 15 ml binding buffer (1×DP buffer/0.4% NP40). After this incubation time the beads were harvested and mixed in a 50 ml falcon tube with MOLT-4 cell lysate at a protein concentration of 5 mg/ml with a total amount of 75 mg protein. The preparation of the lysate was done as described in example 2. Beads and the lysate were incubated for 2 hours at 4° C. After the incubation with the lysate beads were collected by centrifugation as described and transferred to 2 ml columns (MoBiTec, #S10129) and washed with 10 ml 1×DP buffer/0.4% NP40 and 5 ml 1×DP buffer/0.2% NP40. Once the washing buffer had run through the column completely the volume of beads left in the column was calculated (approximately 1000 µl). The beads were resuspended in 4 fold excess of 1×DP-buffer/0.2% NP40 (4 ml) to generate a 20% slurry. For compound elution tests 50 µl of this suspension was added to each well of a 96 well plate (Millipore MultiScreenHTS, MSBVN1210, with lid and 1.2 um hydrophilic low protein binding Durapore membrane). To remove residual buffer the 96 well plate was assembled with Assemble filter and collection plate and this sandwich assembly was spun down for 10 seconds at 800 rpm in a centrifuge. Then 40 µl of elution buffer (1×DP-buffer/0.2% NP40) supplemented with the test compound was added to the beads. Test compounds were prepared by diluting them in dilution buffer starting from 40 fold concentrated stock solution in DMSO. The plate was assembled on the collection plate, fixed on an Eppendorf incubator and incubated for 30 minutes at 4° C. at 650 rpm shaking. To harvest the eluate the 96 well filter plate assembled on the 96 well collection plate was centrifuged for 1 minute at 800 rpm in a table top centrifuge at 4° C. (Heraeus). The eluates were checked for the presence of PI3Kgamma and PI3Kdelta by using a dot blot procedure.

Detection of Eluted PI3K Gamma

The eluted PI3K gamma protein was detected and quantified by a dot blot procedure using an antibody directed against PI3K gamma (Jena Bioscience, #ABD-026S), a fluorescently labeled secondary anti mouse IRDye™ 800 (Rockland, #610-732-124) and the Odyssey Infrared Imaging system from LI-COR Biosciences (Lincoln, Nebr., USA) according to instructions provided by the manufacturer (Schutz-Geschwendener et al., 2004. Quantitative, two-color Western blot detection with infrared fluorescence. Published May 2004 by LI-COR Biosciences, www.licor.com).

Nitrocellulose membranes were treated with 20% ethanol and subsequently washed with 1×PBS buffer. Eluates (as described above) were combined with 12 µl of 4×SDS loading buffer (200 mM Tris-HCl pH6.8, 8% SDS, 40% glycerol, 0.04% Bromphenol blue) and applied to the Nitrocellulose membrane with a BioRad dot blot apparatus (BioRad, #170-6545).

For detection of PI3K gamma the membranes were first blocked by incubation with Odyssey blocking buffer for 1 hour. Blocked membranes were incubated for 16 hours at 4° C. with the first antibody (mouse anti PI3K gamma from Jena Bioscience, ABD-026S) diluted 1:100 in Odyssey blocking buffer supplemented with 0.2% Tween 20. After washing the membrane four times for 5 minutes with 1×PBS buffer containing 0.1% Tween 20 the membrane was incubated for 40 minutes with the detection antibody (anti-mouse IRDye™ 800 from Rockland, 610-732-124), diluted 1:10 000 in Odyssey Blocking Buffer supplemented with 0.2% Tween 20. Afterwards the membrane was washed four times for 5 minutes with 1×PBS buffer/0.1% Tween 20 and once for 5 minutes with 1×PBS buffer. Afterwards the membrane was scanned with the Odyssey reader and data were analysed.

TABLE 5

Preparation of 5x-DP buffer

| Substance: | Stock solution | Final conc. in 1× lysis buffer | Add for 1 l 5× lysis buffer |
|---|---|---|---|
| Tris/HCl pH 7.5 | 1 M | 50 mM | 250 ml |
| Glycerol | 87% | 5% | 288 ml |
| $MgCl_2$ | 1 M | 1.5 mM | 7.5 ml |
| NaCl | 5 M | 150 mM | 150 ml |
| $Na_3VO_4$ | 100 mM | 1 mM | 50 ml |

The 5×-DP buffer was filtered through 0.22 µm filter and stored in 40 ml-aliquots at −80° C. These solutions were obtained from the following suppliers: 1.0 M Tris/HCl pH 7.5 (Sigma, T-2663), 87% Glycerol (Merck, catalogue number 04091.2500); 1.0 M $MgCl_2$ (Sigma, M-1028); 5.0 M NaCl (Sigma, S-5150).

Test Compounds for Elution

The test compounds listed below were used for elution experiments after dilution as described below. Typically all compounds were dissolved in 100% DMSO (Fluka, cat. no 41647) at a concentration of 100 mM or 50 mM. Compounds are stored at −20° C. Dilution of test compound for elution experiments: Prepare 50 mM stock by diluting the 100 mM stock 1:1 with 100% DMSO. For elution experiments further dilute the compound with elution buffer (1×DP-buffer/0.2% NP40). Compounds used for elution:

Compound 1: PI3K inhibitor LY29004 (Tocris 1130; Vlahos et al., 1994, J. Biol. Chem. 269, 5241-5248).

Compound 2: PI3K gamma inhibitor (Calbiochem 528106; AS-605240; Camps et al., 2005, Nature Medicine 11, 936-943).

Compound 3: PI3K gamma inhibitor II (Calbiochem 528108; AS-604850; Camps et al., 2005, Nature Medicine 11, 936-943).

EXAMPLE 4

Competitive Binding Assay for the Identification of PI3K Gamma Interacting Compounds This examples demonstrates a competitive binding assay in which test compounds are added directly into a cell lysate. Test compounds (at various concentrations) and the affinity matrix with the immobilized phenylthiazole ligand 1 were added to lysate aliquots and allowed to bind to the proteins contained in the lysate sample. After the intubation time the beads with captured proteins were separated from the lysate. Bound proteins were then eluted and the presence of PI3K gamma was detected and quantified using a specific antibody in a dot blot procedure and the Odyssey infrared detection system (FIG. 7A). Dose response curves for three compounds were generated (FIG. 7B).

Washing of Affinity Matrix

The affinity matrix as described in example 1 (1.1 ml of dry volume) was washed two times with 15 ml of 1×DP buffer containing 0.4% NP40 and then resuspended in 5.5 ml of 1×DP buffer containing 0.4% NP40 (20% beads slurry).

Preparation of Test Compounds

Stock solutions of test compounds were prepared in DMSO corresponding to a 100fold higher concentration compared to the final desired test concentration (e.g. a 4 mM stock solution was prepared for a final test concentration of 4 µM). This dilution scheme resulted in a final DMSO concentration of 1%. For control experiments (no test compound) a buffer containing 1% DMSO was used so that all test samples contained 1% DMSO.

Compound 1: PI3K inhibitor LY29004 (Tocris 1130; Vlahos et al., 1994, J. Biol. Chem. 269, 5241-5248).

Compound 3: PI3K gamma inhibitor II (Calbiochem 528108; AS-604850; Camps et al., 2005, Nature Medicine 11, 936-943).

Compound 4 (CZC00015387).

Dilution of Cell Lysate

Cell lysates were prepared as described in example 2. For a typical experiment 1 lysate aliquot containing 50 mg of protein was thawed in a 37° C. water bath and then kept at 4° C. To the lysate one volume of 1×DP buffer was added so that a final NP40 concentration of 0.4% was achieved. Then, 1/50 of the final volume of a 50fold concentrated protease inhibitor solution was added (1 tablet of protease inhibitor dissolved in 0.5 ml of 1×DP buffer containing 0.4% NP40; EDTA-free tablet protease inhibitor cocktail from Roche Diagnostics, catalogue number 41647). The lysate was further dilute by adding 1×DP buffer containing 0.4% NP40 so that a final protein concentration of 5 mg/ml was achieved.

Incubation of Lysate with Test Compound and Affinity Matrix

A volume of 100 µl of diluted lysate was dispensed into each well of a 96 well filter plate. Then 1.5 µl of test compound diluted in DMSO was added. For control reactions 1.5 µl DMSO without test compound were used. Then 50 µl of affinity matrix (20% slurry) per well were added. The plate was incubated for 2 hours at 4° C. on a shaker (750 rpm on a Thermomixer, Eppendorf).

The plate was washed using a vacuum manifold instrument (Millipore, MAVM 0960R). Each well was washed 4 times with 400 µl of 1×DP buffer containing 0.4% NP-40 and 2 times with 400 µl with 1×DP buffer containing 0.2% NP-40.

For elution the filter plate was placed on a collection plate and 40 µl of 2× sample buffer (100 mM TrisHCl, pH6.8; 4% SDS; 20% glycerol; 0.02% Bromphenol blue) with DTT (50 mM final concentration) was added to each well. The plates were incubated for 30 minutes at room temperature on a shaker (750 rpm on a Thermomixer, Eppendorf). Subsequently the plates were centrifuged for 2 minutes at 1100 rpm (Heraeus centrifuge) and the eluate was collected in the wells of the collection plate.

Detection and Quantification of Eluted PI3K Gamma

The PI3K gamma protein in the eluates was detected and quantified by a dot blot procedure using a first antibody directed against PI3K gamma (anti PI3K gamma from Jena Bioscience, ABD-026S) and a fluorescently labeled secondary antibody (anti-mouse IRDye™ 800, from Rockland, 610-732-124). The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

The dot blot apparatus was used according to the instructions of the supplier (Bio-Dot microfiltration apparatus, Bio-Rad 170-65). Nitrocellulose membranes (BioTrace NT Nitrocellulose, PALL BTNT30R) were treated with 20% ethanol and subsequently washed with PBS buffer. Per dot 30 µl of eluate sample were applied and left for 30 min before a vacuum pump was applied.

For detection of PI3K gamma the membranes were first blocked by incubation with Odyssey blocking buffer (LI-COR, 927-40000) for 1 hour at room temperature. Blocked membranes were then incubated for 16 hours at 4° C. with the first antibody (anti PI3K gamma from Jena Bioscience, ABD-026S) which was diluted in Odyssey blocking buffer containing 0.2% Tween-20. After washing the membrane four times for 5 minutes with PBS buffer containing 0.1% Tween 20 the membrane was incubated for 40 minutes with the detection antibody (anti-mouse IRDye™ 800 from Rockland, 610-732-124) diluted in Odyssey blocking buffer containing 0.2% Tween-20. Afterwards the membrane was washed four times for 5 minutes each with 1×PBS buffer/0.1% Tween 20 and once for 5 minutes with 1×PBS buffer. The membrane was kept in PBS buffer at 4° C. and then scanned with the Odyssey instrument and signals were recorded and analysed according to the instructions of the manufacturer.

EXAMPLE 5

Compound Profiling of PI3Kdelta Interacting Compounds by Adding Compounds to Cell Lysates or Living Cells This example demonstrates binding assays in which test compounds are added directly into a cell lysate or incubated with living cells (RAW264.7 macrophages).

For the cell lysate competitive binding assay compounds were added to lysate samples and allowed to bind to the proteins contained in the lysate sample. Then the affinity matrix containing the immobilized phenylthiazole ligand was added in order to capture proteins not bound to the test compound. After the incubation time the beads with captured proteins were separated from the lysate by centrifugation. Bead-bound proteins were then eluted and the presence of PI3Kdelta protein was detected and quantified using a specific antibody and the Odyssey infrared detection system.

For the in cell profiling experiment aliquots of life RAW264.7 macrophages were first incubated with compounds for 30 minutes in cell culture medium. During this incubation time the compounds can enter the cells and bind to protein targets within the cells. Then the cells were harvested, cell lysates were prepared and the affinity matrix was added in order to capture proteins not bound to the test compound. After 90 minutes of incubation of the cell lysate with the affinity matrix the beads with the captured proteins were separated from the lysate by centrifugation. Bound proteins were then eluted and the presence of PI3Kdelta was detected and quantified using a specific antibody and the Odyssey infrared detection system.

Both approaches yielded similar results for the cell-permeable reference compound PI-103 (FIG. 8). The two other compounds (compound 5 and 6) interacted with PI3Kdelta in the lysate assay but not significantly in the cell assay. A possible reason for this difference is that the latter two compounds were not sufficiently cell-permeable.

Cell Culture

RAW264.7 macrophages (American Type Culture Collection, Rockville, Md.) were cultured in Dulbecco's modified Eagle's medium (DMEM, 4 mM L-glutamine, 4.5 g/L glucose; Gibco #41965) supplemented with 10% heat-inactivated fetal bovine serum (Gibco #10270) and 1.5 g/L Sodium bicarbonate (Gibco #25080, 7.5% solution) at 37° C. in a humidified atmosphere in the presence of 5% $CO_2$. Macrophages were sub-cultured by scraping the cells from the culture dish in DMEM culture medium using a cell scraper and replating them in fresh culture medium. RAW264.7 macrophages were used for experiments after reaching passage number 3. The cells were washed once with phosphate buffered saline (D-PBS, Gibco #14040), removed from the culture dish in DMEM culture medium and centrifuged at 1,000 rpm at room temperature for 3 minutes. The cell pellet was resuspended in DMEM culture medium and the cell number was determined. $25 \times 10^6$ cells were plated onto one 10 cm-culture dish and incubated for 48 hours in fresh DMEM culture medium until they reached approximately 90% confluence.

A) Compound Profiling in Living Cells

Treatment of Cells with Test Compound

The macrophages were washed with D-PBS buffer and fresh DMEM culture-medium was added. Cells were treated with DMEM culture medium containing 0.2% DMSO (vehicle control) or DMEM culture medium with 10 µM PI-103 (Calbiochem, catalogue number 528100; Knight et al., 2006, Cell 125, 733-747), 10 µM compound 5 or 10 µM compound 6 over a period of 30 minutes. Test compounds were prepared as 20 mM stock solutions in DMSO and further diluted to reach the final concentration of 10 µM compound and 0.2% DMSO in the cell culture medium.

Preparation of Cell Lysates

The culture medium was removed, cells were washed once with D-PBS buffer and 4 ml ice-cold D-PBS buffer was added. Macrophages were removed by gently scraping the cells and resuspending them in D-PBS buffer. The cell suspensions were transferred into 15 ml Falcon tubes and kept on ice. The macrophage suspensions were centrifuged at 1500 rpm 4° C. for 3 minutes in a Heraeus Multifuge. The supernatant was removed and the cell pellets were washed with cold D-PBS buffer. After an additional centrifugation step, the cell pellets were quickly frozen in liquid nitrogen. Cells were thawed on ice and lysed by adding 120 µl 1× lysis buffer (1×DP buffer, 0.8% NP40). The lysates were transferred into 1.5 ml Eppendorf tubes and incubated for 30 minutes rotating at 4° C. and then centrifuged for 10 minutes at 13,200 rpm at 4° C. The supernatants was transferred into ultracentrifuge tubes and centrifuged in a TLA-120.2 rotor at 53,000 rpm (100,000×g) for 1 hour at 4° C. An aliquot of the clarified supernatant was used for protein quantification performing Bradford assay (Biorad Protein Assay dye concentrate, catalogue number 500-0006). The remaining samples were quickly frozen in liquid nitrogen and stored at −80° C. until use in the binding assay.

Dilution of Cell Lysate

Cell lysates were prepared as described below from RAW264.7 macrophages. One lysate aliquot was thawed in a 37° C. water bath and then kept at 4° C. To the lysate one volume of 1×DP buffer containing protease inhibitor (1 tablet of protease inhibitor dissolved in 25 ml of 1×DP buffer or 25 ml of 1×DP buffer containing 0.8% NP40; EDTA-free tablet protease inhibitor cocktail from Roche Diagnostics, catalogue number 41647) was added so that a final NP40 concentration of 0.8% was achieved. The lysate was further diluted by adding 1×DP buffer containing 0.8% NP40 and proteinase inhibitors so that a final protein concentration of 10 mg/ml was achieved.

Washing of Affinity Matrix

The affinity matrix as described in example 1 (0.25 ml of dry bead volume) was washed two times with 10 ml of 1×DP buffer containing 0.2% NP40 and was finally resuspended in 5.0 ml of 1×DP buffer containing 0.2% NP40 (5% beads slurry).

Incubation of Cell Lysate with the Affinity Matrix

A volume of 50 µl of diluted lysate (10 mg/ml protein) was dispensed into each well of a 96 well filter plate. Then 100 µl of affinity matrix (5% slurry) per well were added. The plate was incubated for two hours at 4° C. on a shaker (750 rpm on a Thermomixer, Eppendorf). The plate was washed using a vacuum manifold instrument (Millipore, MAVM 0960R). Each well was washed two times with 220 µl of 1×DP buffer containing 0.4% NP-40. For the elution of proteins the filter plate was placed on a collection plate and 20 µl of 2× sample buffer (100 mM TrisHCl, pH7.4; 4% SDS; 20% glycerol; 0.0002% Bromphenol blue) with DTT (50 mM final concentration) was added to each well. The plates were incubated for 30 minutes at room temperature on a shaker (750 rpm on a Thermomixer, Eppendorf). Subsequently the plates were centrifuged for four minutes at 1100 rpm (Heraeus centrifuge) and the eluate was collected in the wells of the collection plate.

Detection and Quantification of PI3Kdelta

The PI3Kdelta protein in the eluates was detected and quantified by spotting aliquots on a nitrocellulose membrane and detection with a first antibody directed against PI3Kdelta and a fluorescently labeled secondary antibody. The nitrocellulose membranes (BioTrace NT Nitrocellulose, PALL BTNT30R) were pretreated with 20% ethanol and subsequently washed with PBS buffer.

For detection of PI3Kdelta the membranes were first blocked by incubation with Odyssey blocking buffer (LI-COR, 927-40000) for one hour at room temperature. Blocked membranes were then incubated for 16 hours at 4° C. with the first antibody (anti PI3Kdelta, rabbit polyclonal antibody from Santa Cruz, catalogue number sc-7176) which was diluted 1:800 in Odyssey blocking buffer containing 0.2% Tween-20. After washing the membrane four times for seven minutes with PBS buffer containing 0.1% Tween 20 the membrane was incubated for 60 minutes with the detection antibody (goat ant-rabbit IRDye™ 800CW from LICOR, catalogue number 926-32211) diluted 1:2500 in Odyssey blocking buffer containing 0.2% Tween-20 and 0.02% SDS. Afterwards the membrane was washed four times for 5 minutes each with 1×PBS buffer/0.1% Tween 20 and once for five minutes with 1×PBS buffer. The membrane was kept in PBS buffer at 4° C. and then scanned with the Odyssey instrument and signals were recorded and analysed according to the instructions of the manufacturer. The Odyssey Infrared Imaging system from LI-COR Biosciences (Lincoln, Nebr., USA) was operated according to instructions provided by the manufacturer (Schutz-Geschwendener et al., 2004. Quantitative, two-color Western blot detection with infrared fluorescence. Published May 2004 by LI-COR Biosciences, www.licor.com).

B) Compound Profiling in Cell Lysates

Preparation of Cell Lysates

The culture medium was removed, cells were washed once with D-PBS buffer and 4 ml ice-cold D-PBS buffer was added. Macrophages were removed by gently scraping the cells and resuspending them in D-PBS buffer. The cell suspensions were transferred into 15 ml Falcon tubes and kept on ice. The macrophage suspensions were centrifuged at 1500 rpm 4° C. for 3 minutes in a Heraeus Multifuge. The supernatant was removed and the cell pellets were washed with cold D-PBS buffer. After an additional centrifugation step, the cell pellets were quickly frozen in liquid nitrogen. Cells were thawed on ice and lysed by adding 120 µl 1× lysis buffer (1×DP buffer, 0.8% NP40). The lysates were transferred into 1.5 ml Eppendorf tubes and incubated for 30 minutes rotating at 4° C. and then centrifuged for 10 minutes at 13,200 rpm at 4° C. The supernatants was transferred into ultracentrifuge tubes and centrifuged in a TLA-120.2 rotor at 53,000 rpm (100,000×g) for 1 hour at 4° C. An aliquot of the clarified supernatant was used for protein quantification performing Bradford assay (Biorad Protein Assay dye concentrate, catalogue number 500-0006). The remaining samples were quickly frozen in liquid nitrogen and stored at −80° C. until use in the binding assay.

Dilution of Cell Lysate

Cell lysates were prepared as described below from RAW264.7 macrophages. One lysate aliquot was thawed in a 37° C. water bath and then kept at 4° C. To the lysate one volume of 1×DP buffer containing protease inhibitor (1 tablet of protease inhibitor dissolved in 25 ml of 1×DP buffer or 25 ml of 1×DP buffer containing 0.8% NP40; EDTA-free tablet protease inhibitor cocktail from Roche Diagnostics, catalogue number 41647) was added so that a final NP40 concentration of 0.8% was achieved. The lysate was further diluted by adding 1×DP buffer containing 0.8% NP40 and proteinase inhibitors so that a final protein concentration of 10 mg/ml was achieved.

Washing of Affinity Matrix

The affinity matrix as described in example 1 (0.25 ml of dry bead volume) was washed two times with 10 ml of 1×DP buffer containing 0.2% NP40 and was finally resuspended in 5.0 ml of 1×DP buffer containing 0.2% NP40 (5% beads slurry).

Preparation of Test Compounds

For in the lysate competition experiment stock solutions of test compounds were prepared in DMSO corresponding to a 50fold higher concentration compared to the final concentration in the assay (for example a 500 µM stock solution was prepared for a final test concentration of 10 µM). This dilution scheme resulted in a final DMSO concentration of 2% in the assay. For control experiments (no test compound) a buffer containing 2% DMSO was used so that all test samples contained 2% DMSO.

Incubation of Cell Lysate with Test Compound and Affinity Matrix

A volume of 50 µl of diluted lysate (10 mg/ml protein) was dispensed into each well of a 96 well filter plate. Then 3.0 µl of test compound diluted in DMSO was added. For control reactions 3.0 µl DMSO without test compound were used. Then 100 µl of affinity matrix (5% slurry) per well were added. The plate was incubated for two hours at 4° C. on a shaker (750 rpm on a Thermomixer, Eppendorf). The plate was washed using a vacuum manifold instrument (Millipore, MAVM 0960R). Each well was washed two times with 220 µl of 1×DP buffer containing 0.4% NP-40. For the elution of proteins the filter plate was placed on a collection plate and 20 µl of 2× sample buffer (100 mM TrisHCl, pH7.4; 4% SDS; 20% glycerol; 0.0002% Bromphenol blue) with DTT (50 mM final concentration) was added to each well. The plates were incubated for 30 minutes at room temperature on a shaker (750 rpm on a Thermomixer, Eppendorf). Subsequently the plates were centrifuged for four minutes at 1100 rpm (Heraeus centrifuge) and the eluate was collected in the wells of the collection plate.

The detection and quantification of PI3Kdelta was performed as described above.

The invention claimed is:

1. A method for the identification of a phosphoinositide 3-kinase (PI3K) interacting compound, comprising the steps of
    a) providing a protein preparation containing PI3K,
    b) contacting the protein preparation with phenylthiazole ligand 1 immobilized on a solid support under conditions allowing the formation of a phenylthiazole ligand 1-PI3K complex,
    c) incubating the phenylthiazole ligand 1-PI3K complex with a given compound, and
    d) determining whether the compound is able to separate PI3K from the immobilized phenylthiazole ligand 1, thereby identifying the PI3K interacting compound.

2. The method of claim 1, wherein step d) includes the detection of separated PI3K or the determination of the amount of separated PI3K.

3. The method of claim 1, wherein PI3K is PI3K gamma and/or PI3K delta, or wherein the provision of a protein preparation includes the steps of harvesting at least one cell containing PI3K and lysing the cell, or wherein the steps of the formation of the phenylthiazole ligand 1-PI3K complex are performed under essentially physiological conditions.

4. A method for the identification of a PI3K interacting compound, comprising the steps of
    a) providing a protein preparation containing PI3K,
    b) contacting the protein preparation with phenylthiazole ligand 1 immobilized on a solid support and with a given compound under conditions allowing the formation of a phenylthiazole ligand 1-PI3K complex, and
    c) detecting the phenylthiazole ligand 1-PI3K complex formed in step b), wherein a reduced amount of the phenylthiazole ligand 1-PI3K complex formed in the presence of the compound in comparison to the amount of phenylthiazole ligand 1-PI3K complex formed in the absence of the compound indicates that the compound is a PI3K interacting compound.

5. The method of claim 4, wherein in step c) said detecting is performed by determining the amount of the phenylthiazole ligand 1-PI3K complex.

6. The method of claim 5, wherein steps a) to c) are performed with several protein preparations in order to test different compounds.

7. A method for the identification of a PI3K interacting compound, comprising the steps of:
    a) providing two aliquots of a protein preparation containing PI3K,
    b) contacting one aliquot with the phenylthiazole ligand 1 immobilized on a solid support under conditions allowing the formation of a phenylthiazole ligand 1-PI3K complex,
    c) contacting the other aliquot with the phenylthiazole ligand 1 immobilized on a solid support and with a given compound under conditions allowing the formation of a phenylthiazole ligand 1-PI3K complex, and d) determining the amount of the phenylthiazole ligand 1-PI3K complex formed in steps b) and c), wherein a reduced amount of the phenylthiazole ligand 1-PI3K complex formed in step (c) in comparison to that formed in step (b) indicates that the compound is a PI3K interacting compound.

8. A method for the identification of a PI3K interacting compound, comprising the steps of:
a) providing two aliquots each comprising at least one cell containing PI3K,
b) incubating one aliquot with a given compound,
c) harvesting the cells of each aliquot,
d) lysing the cells of each aliquot in order to obtain protein preparations,
e) contacting the protein preparations of each aliquot with the phenylthiazole ligand 1 immobilized on a solid support under conditions allowing the formation of a phenylthiazole ligand 1-PI3K complex, and
f) determining the amount of the phenylthiazole ligand 1-PI3K complex formed in each aliquot in step e), wherein a reduced amount of the phenylthiazole ligand 1-PI3K complex formed in the aliquot incubated with the compound in comparison to the aliquot not incubated with the compound indicates that the compound is a PI3K interacting compound.

9. The method of claim 1, performed as a medium or high throughput screening.

10. The method of claim 1, wherein said compound is selected from the group consisting of synthetic compounds, organic synthetic drugs, and natural small molecule compounds, or wherein the PI3K interacting compound is a PI3K inhibitor, or wherein the solid support is selected from the group consisting of agarose, modified agarose, sepharose beads, latex, cellulose, and ferro- or ferrimagnetic particles, or wherein the phenylthiazole ligand 1 is covalently coupled to the solid support.

11. The method of claim 4, wherein the PI3K is PI3K gamma and/or PI3K delta, or wherein the provision of a protein preparation includes the steps of harvesting at least one cell containing PI3K and lysing the cell, or wherein the steps of the formation of the phenylthiazole ligand 1-PI3K complex are performed under essentially physiological conditions.

12. The method of claim 4, performed as a medium or high throughput screening.

13. The method of claim 4, wherein said compound is selected from the group consisting of synthetic compounds, organic synthetic drugs, and natural small molecule compounds, or wherein the PI3K interacting compound is a PI3K inhibitor, or wherein the solid support is selected from the group consisting of agarose, modified agarose, sepharose beads, latex, cellulose, and ferro- or ferrimagnetic particles, or wherein the phenylthiazole ligand 1 is covalently coupled to the solid support.

14. The method of claim 7, wherein the amount of the phenylthiazole ligand 1-PI3K complex is determined by separating PI3K from the immobilized phenylthiazole ligand 1 and subsequent detection of separated PI3K or subsequent determination of the amount of separated PI3K.

15. The method of claim 7, wherein the PI3K is PI3K gamma and/or PI3K delta, or wherein the provision of a protein preparation includes the steps of harvesting at least one cell containing PI3K and lysing the cell, or wherein the steps of the formation of the phenylthiazole ligand 1-PI3K complex are performed under essentially physiological conditions.

16. The method of claim 7, performed as a medium or high throughput screening.

17. The method of claim 7, wherein said compound is selected from the group consisting of synthetic compounds, organic synthetic drugs, and natural small molecule compounds, or wherein the PI3K interacting compound is a PI3K inhibitor, or wherein the solid support is selected from the group consisting of agarose, modified agarose, sepharose beads, latex, cellulose, and ferro- or ferrimagnetic particles, or wherein the phenylthiazole ligand 1 is covalently coupled to the solid support.

18. The method of claim 8, wherein the amount of the phenylthiazole ligand 1-PI3K complex is determined by separating PI3K from the immobilized phenylthiazole ligand 1 and subsequent detection of separated PI3K or subsequent determination of the amount of separated PI3K.

19. The method of claim 8, wherein the PI3K is PI3K gamma and/or PI3K delta, or wherein the provision of a protein preparation includes the steps of harvesting at least one cell containing PI3K and lysing the cell, or wherein the steps of the formation of the phenylthiazole ligand 1-PI3K complex are performed under essentially physiological conditions.

20. The method of claim 8, performed as a medium or high throughput screening.

21. The method of claim 8, wherein said compound is selected from the group consisting of synthetic compounds, organic synthetic drugs, and natural small molecule compounds, or wherein the PI3K interacting compound is a PI3K inhibitor, or wherein the solid support is selected from the group consisting of agarose, modified agarose, sepharose beads, latex, cellulose, and ferro- or ferrimagnetic particles, or wherein the phenylthiazole ligand 1 is covalently coupled to the solid support.

* * * * *